(12) United States Patent
Samoto et al.

(10) Patent No.: US 9,101,150 B2
(45) Date of Patent: *Aug. 11, 2015

(54) APPLICATION OF REDUCED-FAT SOYBEAN PROTEIN MATERIAL TO SOYBEAN-DERIVED RAW MATERIAL-CONTAINING FOOD OR BEVERAGE

(75) Inventors: Masahiko Samoto, Osaka (JP); Jiro Kanamori, Ibaraki (JP); Masayuki Shibata, Ibaraki (JP); Tsukasa Kiyama, Ibaraki (JP); Masanobu Yanagisawa, Osaka (JP); Mai Kanda, Osaka (JP); Sayuri Kitagawa, Osaka (JP); Yuusuke Shishido, Osaka (JP); Shigeru Ashida, Ibaraki (JP); Takayasu Motoyama, Ibaraki (JP); Kumiko Yoshioka, Ibaraki (JP); Hirofumi Kugitani, Ibaraki (JP); Masashi Asanoma, Osaka (JP); Mitsutaka Kohno, Ibaraki (JP)

(73) Assignee: FUJI OIL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/123,850

(22) PCT Filed: May 23, 2012

(86) PCT No.: PCT/JP2012/063112
§ 371 (c)(1),
(2), (4) Date: Dec. 4, 2013

(87) PCT Pub. No.: WO2012/169348
PCT Pub. Date: Dec. 13, 2012

(65) Prior Publication Data
US 2014/0113866 A1    Apr. 24, 2014

(30) Foreign Application Priority Data

Jun. 7, 2011   (JP) ................................ 2011-126869
Jun. 7, 2011   (JP) ................................ 2011-126870
Dec. 8, 2011   (JP) ................................ 2011-268485
Dec. 12, 2011  (JP) ................................ 2011-270828

(51) Int. Cl.
| | |
|---|---|
| A23C 11/06 | (2006.01) |
| A23C 20/02 | (2006.01) |
| A23J 3/16 | (2006.01) |
| A23L 1/32 | (2006.01) |
| A61K 38/16 | (2006.01) |
| A23C 11/10 | (2006.01) |
| A23L 1/39 | (2006.01) |

(Continued)

(52) U.S. Cl.
CPC ................. *A23C 11/06* (2013.01); *A21D 2/266* (2013.01); *A21D 13/0093* (2013.01); *A21D 13/068* (2013.01); *A23C 11/103* (2013.01); *A23C 11/106* (2013.01); *A23C 20/025* (2013.01); *A23G 1/48* (2013.01); *A23G 3/48* (2013.01); *A23G 9/42* (2013.01); *A23L 1/24* (2013.01); *A23L 1/3216* (2013.01); *A23L 1/39* (2013.01); *A61K 38/168* (2013.01); *A23V 2200/00* (2013.01); *A23V 2200/122* (2013.01)

(58) Field of Classification Search
CPC .. A23C 20/025; A23C 11/103; A23C 11/106; A23C 11/06; A23L 1/24; A23L 1/39; A23L 1/3216; A61K 38/168; A61K 2300/00; A23G 3/48; A23G 9/42; A23G 1/48; A21D 13/0093; A21D 2/266; A21D 13/068; A23V 2200/00; A23V 2200/122; A23V 2200/3324

See application file for complete search history.

(56) References Cited

U.S. PATENT DOCUMENTS

| 4,431,629 A | 2/1984 | Olsen |
| 5,844,086 A | 12/1998 | Murray |

(Continued)

FOREIGN PATENT DOCUMENTS

| CA | 1 151 156 | 8/1983 |
| JP | 57-79841 | 5/1982 |

(Continued)

OTHER PUBLICATIONS

Machine translation of JP 2010-519928 A, pp. 1-47, accessed Jan. 21, 2014.*

(Continued)

*Primary Examiner* — Julie Ha
*Assistant Examiner* — Li Ni Komatsu
(74) *Attorney, Agent, or Firm* — Wenderoth, Lind & Ponack, L.L.P.

(57) ABSTRACT

The present invention addresses the problem of providing a soybean-derived raw material-containing food or beverage that improves problems with flavor and physical properties, such as the grassy smell caused by soybean raw materials, and markedly improves product quality, in a soybean-derived raw material-containing food or beverage using a conventional soybean raw material such soymilk or tofu. Provided are a milk-substitute composition, an egg yolk-substitute composition, and a composition for improving renal function, etc., characterized by including a reduced-fat soybean protein material having a total protein and carbohydrate content relative to dry material of at least 80 wt %, a fat content (as a chloroform/methanol mixed solvent extract) relative to the protein content of less than 10 wt %, and a total campesterol and stigmasterol (as plant-derived sterols) content of at least 200 mg relative to 100 g of fat. Also provided are a variety of soybean-derived raw material-containing food and beverages using these compositions.

20 Claims, 1 Drawing Sheet

(51) Int. Cl.

| | |
|---|---|
| *A23G 3/48* | (2006.01) |
| *A23G 9/42* | (2006.01) |
| *A23L 1/24* | (2006.01) |
| *A21D 2/26* | (2006.01) |
| *A21D 13/00* | (2006.01) |
| *A21D 13/06* | (2006.01) |
| *A23G 1/48* | (2006.01) |

(56) References Cited

U.S. PATENT DOCUMENTS

| | | |
|---|---|---|
| 6,005,076 A | 12/1999 | Murray |
| 6,548,102 B2 | 4/2003 | Fenske et al. |
| 2002/0009460 A1 | 1/2002 | Wakabayashi et al. |
| 2003/0059514 A1 | 3/2003 | Villagran et al. |
| 2010/0112187 A1 | 5/2010 | Crank |
| 2011/0039782 A1 | 2/2011 | Asanoma et al. |
| 2013/0078363 A1 | 3/2013 | Samoto et al. |

FOREIGN PATENT DOCUMENTS

| | | |
|---|---|---|
| JP | 57-115145 | 7/1982 |
| JP | 61-187763 | 8/1986 |
| JP | 4-64660 | 10/1992 |
| JP | 10-165106 | 6/1998 |
| JP | 11-56248 | 3/1999 |
| JP | 11-506619 | 6/1999 |
| JP | 2001-17120 | 1/2001 |
| JP | 2002-20781 | 1/2002 |
| JP | 2002-165568 | 6/2002 |
| JP | 2002-191291 | 7/2002 |
| JP | 2004-141155 | 5/2004 |
| JP | 2005-525083 | 8/2005 |
| JP | 2005-333949 | 12/2005 |
| JP | 2006-204145 | 8/2006 |
| JP | 2009-528847 | 8/2009 |
| JP | 2010-519928 | 6/2010 |
| JP | 2012-16348 | 1/2012 |
| WO | 97/27761 | 8/1997 |
| WO | 98/58554 | 12/1998 |
| WO | 03/022070 | 3/2003 |
| WO | 2006/046686 | 5/2006 |
| WO | 2007/103753 | 9/2007 |
| WO | 2009/110504 | 9/2009 |
| WO | 2011/052793 | 5/2011 |

OTHER PUBLICATIONS

Novozymes-Ku Project 2014, pp. 1-3, published on 2014.*

English Translation of International Preliminary Report on Patentability issued Dec. 19, 2013 in International (PCT) Application No. PCT/JP2012/063112.

International Search Report issued Aug. 14, 2012 in International (PCT) Application No. PCT/JP2012/063112.

Asanoma et al., "An effect of a soybean polar lipid-binding protein (LP: Lipophilic Proteins) for suppressing a progression of early diabetic nephropathy", Food Chemistry, vol. 6 $2^{nd}$, 2008, p. 205, with English abstract.

De Moura et al., "Two-Stage Countercurrent Enzyme-Assisted Aqueous Extraction Processing of Oil and Protein from Soybeans", Journal of the American Oil Chemists' Society, vol. 86, 2009, pp. 283-289.

* cited by examiner

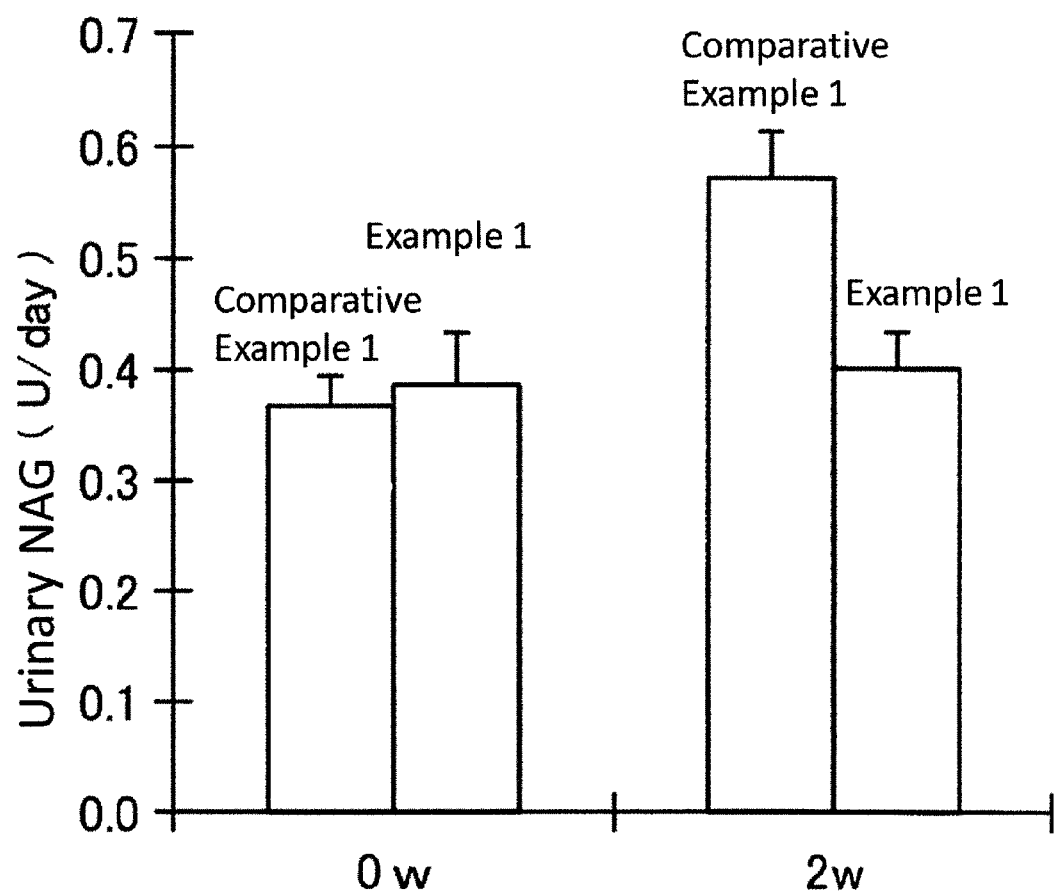

APPLICATION OF REDUCED-FAT SOYBEAN PROTEIN MATERIAL TO SOYBEAN-DERIVED RAW MATERIAL-CONTAINING FOOD OR BEVERAGE

This application is a 371 U.S. National Stage of PCT/JP2012/063112 filed on May 23, 2012; and claims foreign priority to JP 2011-126869 filed on Jun. 7, 2011, JP 2011-126870 filed on Jun. 7, 2011, JP 2011-268485 filed on Dec. 8, 2011, and JP 2011-270828 filed on Dec. 12, 2011.

TECHNICAL FIELD

The present invention relates to a soybean-derived raw material-containing food or beverage in which a soybean material is used as a raw material for various purposes.

More specifically, the present invention relates to a milk substitute composition including soybean-derived ingredient (raw material) and a milk substitute food or beverage prepared by using the composition. In addition, the present invention relates to an egg white substitute composition including soybean-derived raw material and an egg white substitute food prepared by using the composition. Further, the present invention relates to a composition for improving renal function.

BACKGROUND ART

A soybean material such as soymilk, tofu (bean curd) and soybean protein isolate is used as a raw material of various kinds of food or beverage, for example, a milk substitute ingredient, a substitute ingredient for fermented dairy product, an egg white substitute ingredient and an ingredient for improving renal function, in a food or beverage.

A Technology Concerning a Dairy Product Substitution in a Food

A milk raw material such as milk, fresh cream and powdered skim milk has a peculiar milk taste and preference. Therefore, it is widely used for a milk product, for the purpose of topping (decoration), nappe (surface coating), filling or kneading in confectionery, bread, dessert or the like, and for the purpose of adding taste in cooking.

On the other hand, development of vegetable protein raw material as a substitution for milk fat which is animal fat has been conducted from background such as an increase of lifestyle disease by an excessive intake of animal fat, an increase of milk-allergic patient and a price increase of milk raw material.

As a substitute material for milk raw material, application of soybean-derived raw material such as tofu, soymilk and powdered soybean protein isolate is considered (e.g., soymilk whipped cream of Patent Document 1). However, taste degradation due to oxidization becomes a problem in the case of using whole fat soy flour, soymilk or tofu because soybean contains a fat including a lot of amount of non-saturated fatty acid such as linoleic acid and linolenic acid. Therefore, defatted soybean in which fat is removed with an organic solvent or the like, or defatted soymilk or powdered soybean protein isolate which is prepared from the defatted soybean is produced, and a part of these products is used as a substitute raw material (e.g., Patent Document 2, Patent Document 3 etc.). However, these products lack good taste of soybean compared to whole fat soybean. In addition, taste degradation due to oxidization cannot be sufficiently suppressed even after defatting.

Although food or drink such as confectionery, dessert, beverage, soup and sauce prepared from these soybean-derived raw materials has a healthier image, it has a drawback that a peculiar taste of raw vegetation and astringent taste derived from soybean or processed smell generated in the process generates an adverse effect on the taste of the food or drink. Therefore, various improvements such as adding a taste masking agent have been considered. However, it is difficult to suppress an unpleasant taste. And, there has been a room for improvement of vegetable raw material as a substitute material for milk raw material.

A Technology Concerning a Substitution for an Egg White in a Food

Next, egg, milk and soybean, which account for 95% or more of allergic cause with food, called as three major food allergens are used as a raw material of many kinds of processed foods. Therefore, patient who has the allergy to these foods receives the limitation to the intake of extremely a lot of foods, and is constrained to receive pain every day. In order to inhibit an allergic reaction of the patient who has the allergy to food, there is no alternative but to cure the allergy itself or intake food which includes no allergen. However, treatment of allergy requires time of each year and has a low success rate. Thus, substitution food for food-allergic patient, which does not include a food including allergen but can give a texture similar to the food, has been developed.

Patent Document 4 discloses a dressing which does not include egg yolk but includes starch octenylsuccinate. However, modified starch associated with chemical processing is avoided, and has a problem that an intended use thereof is restricted. Patent Document 5 discloses a baking powder mix in which soybean protein is used for the replacement of egg white. However, the soybean protein requires ultrafiltration, and it lacks practicality.

Patent Document 6 discloses an egg-free mayonnaise having baking resistance. However, concern of long-term stability remains in the product because protein is not positively used.

A Technology Concerning an Improvement of Renal Function

Next, Patent Document 7 describes a soybean protein material for patients with renal disease.

PRIOR ART DOCUMENTS

Patent Documents

Patent Document 1: JP H4-64660 A
Patent Document 2: JP 2005-525083 A
Patent Document 3: JP 2002-191291 A
Patent Document 4: JP 2005-333949 A
Patent Document 5: JP S57-115145 A
Patent Document 6: JP 2001-17120 A
Patent Document 7: WO 2009/110504 A1

SUMMARY OF THE INVENTION

Problems to be Solved by the Invention

An object of the present invention is to provide a soybean-derived raw material-containing food or beverage having significantly improved quality and overcoming defects relating to taste and physical property in conventional food or beverage containing soybean material such as soymilk and tofu, for example, taste of raw vegetation derived from the soybean material. Hereinafter, more specific problems will be described.

First Problem

As for the technology concerning the substitution for a milk raw material in a food, as above mentioned, any conventional method cannot provide soybean-derived material which does not have taste of raw vegetation derived from soybean and does not show taste degradation over time and is sufficient for using as substitution for milk raw material.

Thus, one of the problems of the present invention is to provide a soybean-derived milk substitute composition which does not have a taste of raw vegetation peculiar to soybean and processed smell generated in the process, but has good soybean taste and can be widely used as milk substitute raw material. In addition, it is also to provide a milk substitute food or beverage which is prepared by using the composition and is easy to acceptable by consumer and has comfortable taste as a food.

Second Problem

As for the technology concerning the substitution for an egg white in a food, among the three major food allergens, a part of substitute food for cow milk (milk) and soybean is developed. However, no substitute material for egg, which is most major allergen, has sufficient quality though application of egg is wide-ranging.

Thus, one of the problems of the present invention is to provide a food material which is substitution for egg and enables to prepare a lot of foods conventionally produced or cooked by using egg.

Third Problem

As for the technology concerning an improvement of renal function, one of the problems of the present invention is a composition for improving renal function having an improved taste.

Means for Solving the Problems

As means for solving the above mentioned problems, the present invention provides the following means for solving the problems.

(1) A milk substitute composition comprising a reduced-fat soybean protein material comprising a protein and a carbohydrate at a total content of 80 wt % or more in terms of dry basis, a fat at a content of less than 10 wt % (as an extract with a chloroform/methanol mixed solvent) relative to the protein content, and campesterol and stigmasterol as phytosterols at a total content of 200 mg or more relative to 100 g of the fat;

(2) A milk substitute composition comprising a reduced-fat soybean protein material as recited in (1), wherein a total content of campesterol and stigmasterol as phytosterols in the reduced-fat soybean protein material is 230 mg or more relative to 100 g of the fat, and LCI value of the reduced-fat soybean protein material is 40%, or less;

(3) A milk substitute food or beverage prepared by using the milk substitute composition as recited in (1);

(4) A milk substitute food or beverage prepared by using the milk substitute composition as recited in (2);

(5) A lactic acid-fermented soybean food or beverage, which is obtained by fermenting a raw material comprising the milk substitute composition as recited in (1) with a lactic acid bacterium;

(6) A lactic acid-fermented soybean food or beverage, which is obtained by fermenting a raw material comprising the milk substitute composition as recited in (2) with a lactic acid bacterium;

(7) An egg white substitute composition comprising the reduced-fat soybean protein material as recited in (1);

(8) An egg white substitute composition comprising the reduced-fat soybean protein material as recited in (2);

(9) An egg white substitute food or beverage prepared by using the egg white substitute composition according to (7);

(10) An egg white substitute food or beverage prepared by using the egg white substitute composition according to (8);

(11) A composition for improving renal function, comprising the reduced-fat soybean protein material as recited in (1);

(12) A composition for improving renal function, comprising the reduced-fat soybean protein material as recited in (2);

(13) A food comprising the composition for improving renal function according to (11);

(14) A food comprising the composition for improving renal function according to (12);

(15) A process for producing a soybean-derived raw material-containing food or beverage, which comprises using the reduced-fat soybean protein material as recited in (1) or (2) as a substitute for a part or all of raw material selected from a group consisting of milk raw material and egg white, or as a composition for improving renal function.

Hereinafter, the reduced-fat soybean protein material recited in the above (1) is called as "this reduced-fat soybean protein material".

In addition, the present invention also provides more specific means for solving the problems based on the above specific first to third problems as follows.

First Aspect of the Invention

In order to solve the first problem relating to the technology concerning a substitution for a milk raw material in a food, the present inventors intensively studied. As a result, they have found a process of obtaining soymilk having little fat content from soybean without using organic solvent. They have also found that a reduced-fat soybean protein material such as said soymilk and soybean protein isolate prepared from the material is novel composition having specific ingredient composition, and that taste of the material is good natural soybean taste without uncomfortable taste and taste degradation with time like a conventional soybean material. In addition, they have found that this reduced-fat soybean protein material is suitable for a milk substitute food or beverage as a milk substitute composition. The first aspect of the invention has been completed on the basis of these findings.

That is, the first aspect of the invention provides the following (1) to (12):

(1) A milk substitute composition comprising this reduced-fat soybean protein material;

(2) The milk substitute composition according to (1), wherein the soybean protein material is soymilk or soybean protein isolate;

(3) The milk substitute composition according to (1) or (2), which is powdered milk type, concentrated milk type or liquid milk type;

(4) The milk substitute composition according to any one of (1) to (3), further comprising fat as an oil-in-water emulsion;

(5) The milk substitute composition according to any one of (1) to (4), further comprising sugar;

(6) A milk substitute food or beverage prepared by using the milk substitute composition according to any one of (1) to (5);

(7) The milk substitute food or beverage according to (6), which is dairy product, sauce, bakery product, confectionery or high nutrient liquid food;

(8) The milk substitute food or beverage according to (7), wherein the dairy product is yogurt, lactic acid fermented beverage, cream, ice cream, cheese, margarine or infant formula;

(9) The milk substitute food or beverage according to any one of (6) to (8), which is fat-free or low fat type;

(10) A lactic acid-fermented soybean food or beverage, which is obtained by fermenting a raw material comprising the milk substitute composition according to any one of (1) to (5) with a lactic acid bacterium;

(11) A process for producing a milk substitute food or beverage, comprising using this reduced-fat soybean protein material as a part or all of milk raw material;

(12) Use of this reduced-fat soybean protein material as a milk substitute composition.

Second Aspect of the Invention

In order to solve the second problem relating to the technology concerning a substitution for an egg white in a food, the present inventors intensively studied. As a result, they have found that a reduced-fat soybean protein material obtainable by special preparation process has good function of substituting egg white. The second aspect of the invention has been completed on the basis of these findings.

That is, the second aspect of the invention provides the following (1) to (9):

(1) An egg white substitute composition comprising this reduced-fat soybean protein material;

(2) The egg white substitute composition according to (1), wherein the soybean protein material is soymilk or soybean protein isolate;

(3) The egg white substitute composition according to (1) or (2), further comprising fat as an oil-in-water emulsion;

(4) The egg white substitute composition according to (1) or (2), which is solution containing air bubble or fluid containing air bubble;

(5) The egg white substitute composition according to (1) or (2), which is fluid or gel-like material;

(6) The egg white substitute composition according to any one of (1) to (5), further comprising sugar;

(7) An egg white substitute food or beverage prepared by using the egg white substitute composition according to any one of (1) to (6);

(8) The egg white substitute food or beverage according to (7), which is meringue-like food, dressing-like food, mayonnaise-like food, gel-like food or bakery product such as confectionery;

(9) A process for producing an egg white substitute food or beverage, comprising using this reduced-fat soybean protein material as a part or all of egg white raw material.

Third Aspect of the Invention

In order to solve the third problem relating to the technology concerning an improvement of renal function, the present inventors intensively studied. Patent Document 1 describes that "non-7S and non-11S acid-precipitable soybean protein" has a strong urinary albumin lowering action. However, the "non-7S and non-11S acid-precipitable soybean protein" is prepared from defatted soybean as a raw material, and therefore, it may have a taste derived from defatted soybean.

The present inventors intensively studied in the above circumstance. As a result, they have found that a reduced-fat soybean protein material prepared by specific process without using defatted soybean as a raw material has extremely good taste and effect of improving renal function. The third aspect of the invention has been completed on the basis of these findings.

That is, the third aspect of the invention provides the following (1) to (3):

(1) A composition for improving renal function, comprising this reduced-fat soybean protein material;

(2) A food comprising the composition for improving renal function according to (1);

(3) A process for producing a food, comprising using the composition for improving renal function according to (1).

Effect of the Invention

According to the first aspect of the invention, vegetable composition as a substitute material for milk raw material having good taste can be provided by using novel this reduced-fat soybean protein material, where the material does not have taste of raw vegetation and processed smell, which is problems of conventional soybean, and has little taste degradation, and where the material has refreshing soybean taste. Such a composition has been not able to be achieved by a conventional soybean material.

According to the second aspect of the invention, an egg white substitute composition or an egg white substitute food or beverage can be obtained without using egg.

A composition for improving renal function according to the third aspect of the invention has good taste and a function of improving renal function. Therefore, various foods having good taste and showing an effect of improving renal function can be easily obtained by using the composition.

BRIEF DESCRIPTION OF DRAWINGS

FIG. 1 A FIGURE showing urinary NAG activity of rat after 2 weeks feeding.

MODE FOR CARRYING OUT THE INVENTION

Any of a milk substitute composition according to the first aspect of the invention, an egg white substitute composition according to the second aspect of the invention and a composition for improving renal function according to the third aspect of the invention commonly include novel "reduced-fat soybean protein material" described in the following. More specifically, a content described in the specification of Japanese patent application (Japanese patent application No. 2011-108598) is incorporated herein. Hereinafter, the reduced-fat soybean protein material which is common specific technical feature of the first to third aspects of the present invention will be described.

<Reduced-Fat Soybean Protein Material>

The reduced-fat soybean protein material used in the present invention contains a protein based on glycinin and β-conglycinin as major component. In the case of the reduced-fat soymilk, relatively large amount of soluble component such as sugar and ash is contained. On the other hand, fiber is removed, fat including both neutral lipid and polar lipid is reduced, in addition, LP content such as lipoxygenase protein content is low.

That is, the reduced-fat soybean protein material includes a protein and a carbohydrate at a total content of 80 wt % or more in terms of dry basis, a fat at a content of less than 10 wt % (as an extract with a chloroform/methanol mixed solvent) relative to the protein content, and campesterol and stigmasterol as phytosterols at a total content of 200 mg or more relative to 100 g of the fat.

A typical example of a soybean protein material includes a soymilk, and the soybean protein material other than soymilk includes a soybean protein material in which purity of protein is improved from said soymilk as a raw material, more specifically, soybean protein isolate in which purity of protein is improved by removing soluble components such as sugar and ash from soymilk or fractionated soybean protein in which purity of glycinin or β-conglycinin is improved by further fractionating protein from the soymilk or the soybean protein isolate. The soybean protein isolate or the fractionated soybean protein can be prepared by a well known method.

(Carbohydrate)

Sugar and protein are major component of this reduced-fat soybean protein material and constituent a large part of dry matter. Total content of protein and carbohydrate (a content of dry matter excluding fat, protein and ash) in the reduced-fat soybean protein material is 80 wt % or more, preferably 85 wt % or more in terms of dry basis. Remaining dry matter consists of ash and a slight amount of fat, and ash content is usually 15 wt % or less, preferably 10 wt % or less. Although fiber is included in carbohydrate, fiber is removed from the reduced-fat soybean protein material of the present invention. Therefore, fiber content is small, more specifically, 3 wt % or less, preferably 2 wt % or less.

(Protein)

A protein content of this reduced-fat soybean protein material can be in a range from 30 to 99 wt % in terms of dry basis. When the soybean protein material is soymilk, a lower limit of the protein content is usually 45 wt % or more, or 50 wt % or more, or 55 wt % or more, and an upper limit can be 70 wt % or less, or 65 wt % or less. Depending on a process such as fractionation of protein and adding other component, protein content can be in a range from 30 wt % or more to less than 45 wt %. In addition, when the reduced-fat soybean protein material is a soybean protein isolate in which purity of protein is improved by further purifying a soymilk, a lower limit of protein content can be more than 70 wt % or 80 wt % or more, and an upper limit can be 99 wt % or less, or 95 wt % or less.

Analysis of Protein Content

A protein content in the present invention is calculated by multiplying a nitrogen content measured by Kjeldahl method by a nitrogen coefficient of 6.25.

Composition Analysis of Each Component of the Protein

Each component composition of protein in this reduced-fat soybean protein material can be analyzed by SDS polyacrylamide gel electrophoresis (SDS-PAGE). A hydrophobic interaction and a hydrogen bond between protein molecules and an intermolecular disulfide bond are broken by action of SDS as a surfactant and mercaptoethanol as a reductant, and thereby, the negatively charged protein molecule shows the electrophoresis distance according to peculiar molecular weight. In the result, an electrophoretic pattern peculiar to each protein is obtained. The analysis can be carried out by staining SDS gel with Coomassie brilliant blue (CBB) as a dye after the electrophoresis, and then calculating a proportion of density of band that corresponds to each protein molecule to density of band of total protein by using densitometry.

(Lipoxygenase Protein)

It is also a quite characteristic of this reduced-fat soybean protein material that a content of lipoxygenase protein which is generally easily extracted due to its water-solubility is extremely low, and it is 1% or less, preferably 0.5% or less relative to total protein in the reduced-fat soybean protein material.

When a conventional nature soybean (NSI of 90 or more) is used as a raw material, lipoxygenase protein is extracted to water-soluble fraction by water extraction because the lipoxygenase protein is soluble state. On the other hand, lipoxygenase protein is remained in the insoluble fraction because the lipoxygenase protein is denatured and insolubilized in the raw material soybean by heat treatment.

There is an advantage that soymilk in which fat content is maintained to extremely low level can be obtained because a rate of lipoxygenase protein in protein of the reduced-fat soybean protein material is extremely low.

Normally, there are three types of lipoxygenase protein, L-1, L-2 and L-3. A content of each lipoxygenase protein can be calculated from density of band that corresponds to each lipoxygenase protein by using the above electrophoresis.

(Lipophilic Proteins: LP)

It is one of characteristics of this reduced-fat soybean protein material of the present invention that LP content is smaller than conventional soybean material among types of protein. The lipophilic proteins refer to a group of minor acid-precipitable soybean proteins other than glycinin (7S globulin) and β-conglycinin (11S globulin) among acid-precipitable soybean proteins of a soybean, and are accompanied by a lot of polar lipids such as lecithin and glycolipid. Hereinafter, the lipophilic proteins are simply abbreviated as "LP" in some cases.

Since LP is a mixture of various proteins, it is difficult to specify all of respective proteins and LP content. However, LP content can be estimated by determining the following LCI (Lipophilic Proteins Content Index) value.

In this case, LCI value of the protein in this reduced-fat soybean protein material is usually 40% or less, more preferably 38% or less, further preferably 36% or less.

When a conventional nature soybean (NSI of 90 or more) is used as a raw material, LP is extracted to water-soluble fraction by water extraction because the LP is soluble state. On the other hand, LP is remained in the insoluble fraction because the LP is denatured and insolubilized in the raw material soybean by heat treatment.

There is an advantage that soymilk in which fat content is maintained to extremely low level can be obtained because a rate of LP in protein of this reduced-fat soybean protein material is extremely low.

Method of Estimating LP Content and Measuring LCI Value (a) As the main proteins in respective proteins, an a subunit and an α' subunit (α+α') are selected for 7S, an acidic subunit (AS) is selected for 11S, and a 34 kDa protein and lipoxygenase (P34+Lx) are selected for LP. Then, a staining ratio among the selected proteins on SDS-PAGE is determined. Electrophoresis can be performed under the condition shown in Table 1.

(b) $X (\%)=(P34+Lx)/\{(P34+Lx)+(\alpha+\alpha')+AS\}\times 100(\%)$ is calculated.

(c) Since the LP content of an isolated soybean protein prepared from a low-denatured defatted soybean is about 38% as measured by the fractionation methods of the above-described Methods 1 and 2 before heat-sterilization, (P34+Lx) is multiplied by a correction coefficient $k^*=6$ so that X becomes 38(%).

(d) That is, an estimated LP content (Lipophilic Proteins Content Index, hereinafter abbreviated as "LCI") is calculated by the equation below.

TABLE 1

| | |
|---|---|
| Application amount: | 10 μl of a protein 0.1% sample solution per well |
| Well width: | 5 mm |
| Well volume: | 30 μl |
| Staining solution: | Coomassie Brilliant Blue (CBB) 1 g, methanol 500 ml, glacial acetic acid 70 ml (after CBB is completely dissolved in methanol, acetic acid and water are added to 1 L) |
| Staining time: | 15 hours |
| Discoloration time: | 6 hours |
| Densitometer: | GS-710 Calibrated Imaging Densitometer/Quantity One Software Ver.4.2.3 (Bio Rad Japan Co. Ltd) Scanning width: 5.3 mm, Sensitivity: 30 |

$$LCI(\%) = \frac{k^* \times (P34 + Lx)}{k^* \times (P34 + Lx) + (\alpha + \alpha') + AS} \times 100$$

$K^*$: Correction coefficient(6)

$P34$: LP main component, 34$kDa$ protein $Lx$: LP main component, lipoxygenase $\alpha$: 7$S$ main component, $\alpha$ subunit $\alpha'$: 7$S$ main component, $\alpha'$ subunit $AS$: 11$S$ main component, acidic subunit (Fat)

This reduced-fat soybean protein material contains fat at a value lower than a ratio of fat content/protein content of soy flour as a raw material. And, both neutral lipid content and polar lipid content in the reduced-fat soybean material are low. On the other hand, conventional reduced-fat soymilk is obtained by water extraction of defatted soybean defatted with hexane, and contains much more polar lipid which is not removed.

Therefore, a fat content of this reduced-fat soybean protein material is determined by extracting with a mixed solvent of chloroform and methanol at a volume ratio of 2:1 at atmospheric boiling point for 30 minutes, and calculating fat content with assuming the obtained extract as a total fat. As a solvent extraction equipment, "Soxtec" manufactured by FOSS Co. can be used. Hereinafter, the above measurement method is also called as "chloroform/methanol mixed solvent extraction method".

A fat content of this reduced-fat soybean protein material relative to protein content is less than 10 wt %, preferably less than 9 wt %, more preferably less than 8 wt %, further preferably less than 5 wt %, further more preferably 4 wt % or less. Also, 3 wt % or less is possible. That is, it is one of quite characteristics that total fat including neutral lipid and polar lipid is far less than protein. A conventional defatted soymilk extracted from defatted soybean defatted by using organic solvent contains less neutral lipid, but fat content relative to protein is about 5 to 6 wt % because some of polar lipid is extracted. That is, fat content of this reduced-fat soybean protein material is reduced similarly or more than conventional defatted soymilk obtained by using organic solvent.

In addition, fat content in terms of dry basis is also 5 wt % or less, preferably 3 wt % or less, more preferably 2 wt % or less, further preferably 1.5 wt % or less.

(Phytosterol)

It is one of characteristics that this reduced-fat soybean protein material has much higher phytosterol content relative to fat content than conventional defatted soymilk.

A phytosterol is contained in soybean seed at about 0.3 wt %, and includes sitosterol, campesterol, stigmasterol and the like. These phytosterols contained in soybean are largely transferred to soybean oil due to their low polarity when soybean oil is extracted with organic solvent such as hexane, and then the phytosterols are removed through a process of purifying the soybean oil. Therefore, defatted soybean contains very small amount of phytosterol.

On the other hand, in this reduced-fat soybean protein material, it is found that campesterol and stigmasterol as phytosterols which are more lipophilic and water-insoluble are remained at especially large amount in spite of low content of neutral lipid and polar lipid. Thus, it is very difficult to increase a phytosterol content relative to fat content in a reduced-fat soybean protein material by a method other than adding separately. The present invention has an advantage that a soybean protein material, which contains little amount of fat and a large amount of phytosterol, can be provided.

Total content of campesterol and stigmasterol in a reduced-fat soybean protein material which is prepared by using a defatted soybean defatted with organic solvent such as hexane is about 40 to 50 mg per 100 g of fat. On the other hand, this reduced-fat soybean protein material has much higher content, for example, 200 mg or more per 100 g of fat, preferably 230 mg or more, more preferably 400 mg or more, further preferably 450 mg or more, further more preferably 500 mg or more per 100 g of fat.

A content of these phytosterols are determined by general method, for example, calculating from ratio of peak area of sample to that of reference standard determined by using chromatography after an extraction with organic solvent.

For example, phytosterol content can be determined based on a method for quantitating sterol of Japan Food Research Laboratories (see annex flow chart of No. 11014761 analytical method). In particular, 1.2 g of sample is dispersed to 50 ml of ethanol solution of potassium hydroxide (1 mol/L), and then carrying out saponification, and then extracting unsaponifiable matter to ether layer by adding 150 ml of water and 100 ml of diethyl ether, further adding 50 ml of diethyl ether twice to extract. The diethyl ether layer containing unsaponifiable matter is water-washed and subjected to dewatering filtration and then evaporated. The obtained extract is applied to column (silica gel cartridge column), and washed with 10 ml of diethyl ether:hexane (8:92) solution, and then eluted with 25 ml of diethyl ether:hexane (20:80) solution. To the eluted solution is added 0.5 mg of 5$\alpha$-cholestane as internal standard, and then evaporated. To the resultant sample is added 5 ml of hexane, and then applied to gas chromatograph (with hydrogen flame ionization detector) to detect an objective phytosterol. The gas chromatography can be carried out according to the following conditions.

<Operating Conditions of Gas Chromatograph>

Model: GC-2010 (Shimadzu Corporation)

Detector: FID

Column: DB-1 (J&W SCIENTIFIC) 00.25 mm×15 m, Film thickness 0.25 μm

Temperature: Inlet 290° C., Detector 290° C., Column 240° C., increased to 280° C. at a rate of 3° C./min Sample injection system: Split (split ratio 1:30)

Flow rate: Helium (as carrier gas) 2.3 ml/min, Helium (as make up gas) 30 ml/min Pressure: Hydrogen 40 ml/min, Air 400 ml/min (Isoflavones)

It is one of characteristics that this reduced-fat soybean protein material contains relatively large amount of isofravone. More specifically, 0.10 wt % or more in terms of dry basis is preferable. Isoflavone content can be determined according to an analytical method described in "Standards and criteria for food containing isoflavone (public announcement No. 50, revised edition)" (Japan Health and Nutrition Food Association, issued on Mar. 6, 2009). In the present invention isoflavone content refers to an equivalent amount as a glycoside.

(Dry Matter)

When this reduced-fat soybean protein material is reduced-fat soymilk and liquid form, dry matter in the reduced-fat soybean protein material is usually, but not limited to, around 3 to 20 wt %. For example, the reduced-fat soybean protein material can be a liquid form with low viscosity obtained by adding water, a form with high viscosity obtained by condensation such as vacuum concentration and freeze concentration and a powder form obtained by powderization such as spray drying and lyophilization.

(Aspect of Producing the Reduced-Fat Soybean Protein Material)

The reduced-fat soymilk used in the present invention and other soybean protein materials prepared from the reduced-fat soymilk can be obtained by adding water to a fat-containing soybean which contains a fat at a content of 15 wt % or more in terms of dry basis and which has Nitrogen Solubility Index (hereinafter, refers to "NSI") in the range from 20 to 77, preferably from 20 to 70, to prepare a suspension liquid, and then subjecting the suspension liquid to a solid-liquid separation to transfer neutral lipid and polar lipid to an insoluble fraction, and then removing the insoluble fraction, and then recovering a soluble fraction including protein and sugar. Hereinafter, an aspect of the production method will be explained.

Soybean Raw Material and Processing Thereof.

A fat-containing soybean such as whole fat soybean, partially defatted soybean is used as soybean raw material for producing this reduced-fat soybean protein material. The partially defatted soybean includes one obtained by subjecting whole fat soybean to a physical extraction treatment such as press extraction for partially defatting. Generally, whole fat soybean contains about 20 to 30 wt % of fat in terms of dry basis. There are also special soybeans which contain 30 wt % or more of fat. The fat-containing soybean used for the present invention is not limited, but soybean having 15 wt % or more, preferably 20 wt % or more of fat is preferable. A form of the raw material can include halved, grits or powder form.

When fat content is too low because of too much defatting, it is difficult to obtain the reduced-fat soymilk rich in phytosterols while the obtained reduced-fat soymilk has low fat content. Especially, defatted soybean having 1 wt % or less of neutral lipid content obtained by solvent extraction such as hexane extraction is not preferable because good soybean taste is deteriorated.

Generally, the above described fat-containing soybean is soluble and has 90 or more of NSI because most of the constituent proteins are nature and soluble. However, a modified soybean, which is subjected to a process so that NSI of the modified soybean is 20 to 77, preferably 20 to 70, is preferable. A lower limit of the NSI is more preferably 40 or more, further preferably 41 or more, further more preferably 43 or more, most preferably 45 or more. An upper limit of the NSI is more preferably less than 75, further preferably less than 70. In addition, soybean having low NSI such as less than 65, less than 60 and less than 58 can be used.

Such a modified soybean is obtained by carrying out a processing treatment such as heat treatment and alcohol treatment. The processing treatment includes, but not limited to, heat treatment such as dry heat treatment, steam treatment, superheated steam treatment and microwave treatment, hydrous ethanol treatment, high-pressure treatment and combination thereof.

When NSI is high value such as 80 or more, separation efficiency between fat and protein is reduced, and thereby, increasing fat content in the reduced-fat soybean protein material. In addition, as for the taste, taste of raw vegetation becomes strong.

When heat treatment with superheated steam is carried out, treatment condition cannot be specified for all cases since it will differ depending on manufacturing environment, but appropriate condition for obtaining a modified soybean having the above range of NSI can be determined without special difficulty, for example, heating with superheated steam at about 120 to 250° C. for 5 to 10 minutes. As simple means, commercially available soybean having the above range of NSI can be used.

NSI can be expressed as ratio (wt %) of water-soluble nitrogen (crude protein) to total protein and determined by a prescribed method. In the present invention, NSI is determined by the following method.

To 2.0 g of sample is added 100 ml of water. The mixture is stirred at 40° C. for 60 minutes, and then centrifuged at 1400×g for 10 minutes to obtain supernatant 1. To the residual precipitate is added 100 ml of water. The mixture is stirred at 40° C. for 60 minutes, and then centrifuged at 1400×g for 10 minutes to obtain supernatant 2. The supernatant 1 and supernatant 2 are combined, and water is added to 250 ml. After filtering the mixture with No. 5A filter paper, nitrogen in the filtrate is determined by Kjeldahl method. At the same time, nitrogen in the sample is determined by Kjeldahl method. NSI is the ratio of nitrogen in the filtrate (soluble nitrogen) to total nitrogen in the sample, and expressed as wt %.

The above modified soybean is preferably subjected to a dry or wet tissue destruction treatment such as grinding, crushing and depressing before a water extraction. The soybean can be swelled by water immersion or steaming before the tissue destruction treatment. By the swelling, the amount of energy required to the tissue destruction can be reduced and component having unpleasant taste such as whey protein and oligosaccharide can be eluted and removed, as well as, extraction ratio of globulin protein (in particular, glycinin and β-conglycinin) having high water retention ability and gelling ability to total protein can be increased, that is, transfer ratio of the globulin protein into the soluble fraction can be increased.

Water Extraction from Soybean Raw Material

Water extraction is carried out by adding water at about 3 to 20 times by weight, preferably 4 to 15 times by weight relative to an amount of fat-containing soybean, and thereby preparing a suspension of the fat-containing soybean. When adding ratio of water is high, extraction rate of water-soluble component is high and good separation can be obtained. But, when the adding ratio is too high, a concentration is necessary and thereby increasing in cost. In addition, when water extraction is repeated twice or more, extraction rate of water-soluble component can be improved.

An extraction temperature is not limited. When the temperature is high, an extraction rate of water-soluble component can be improved, but fat also tends to be soluble, and thereby, fat content in the reduced-fat soymilk becomes high. Therefore, the extraction temperature is preferably 70° C. or lower, more preferably 55° C. or lower. Alternatively, the water extraction can be carried out at 5 to 80° C., more preferably 50 to 75° C.

Concerning an extraction pH (pH of a soybean suspension after adding water), as is the case in the extraction temperature, when the pH is high, an extraction rate of water-soluble component can be improved, but fat also tends to be soluble, and thereby, fat content in the reduced-fat soymilk becomes high. On the other hand, when the pH is too low, an extraction rate of protein tends to be low. More specifically, the extraction can be carried out with adjusting a lower limit of pH to pH 6 or higher, pH 6.3 or higher, or pH 6.5 or higher. In addition, the extraction can be carried out with adjusting an upper limit of pH to pH 9 or lower, pH 8 or lower, or pH 7 or lower from a standpoint of increasing a separation efficiency of fat. Alternatively, the extraction can be carried out with adjusting pH to more alkaline, pH 9 to 12 from a standpoint of increasing an extraction rate of protein.

Solid-Liquid Separation after the Water Extraction

After the water extraction, suspension of the fat-containing soybean is subjected to a solid-liquid separation such as centrifugation and filtration. In this case, it is important that most of fat including neutral lipid as well as polar lipid is not eluted to water-extract, but transferred to a fraction of insolubilized protein and fiber as a precipitate (insoluble fraction). More specifically, 70 wt % or more of fat of fat-containing soybean is transferred to the precipitate. In addition, a small amount of fat is eluted to a supernatant when carrying out the extraction. However, it is different from a fat which is finely emulsified in soymilk, and can easily be floated and separated by centrifuging at 15,000×g or less or about 5,000×g or less. In this respect, it is preferable to use a centrifuge. In addition, an ultracentrifuge at 100 thousand×g or more can be used depending on facilities. However, in the case of this reduced-fat soybean protein material used in the present invention, it can be carried out without using the ultracentrifuge.

In addition, demulsifier can be added during or after the water extraction to improve fat separation from soymilk. The demulsifier is not limited, for example, a demulsifier described in Patent Document 2 described in the specification of Japanese patent application (Japanese application No. 2011-108598) can be used. Further, the present invention can be carried out without using the demulsifier.

Not only neutral lipid but also polar lipid can be transferred to an insoluble fraction by the solid-liquid separation after the water extraction. A fraction of the reduced-fat soymilk can be obtained by recovering a soluble fraction.

In the case of using centrifugation as solid-liquid separation, both two phase separation system and three phase separation system can be used. In the case of using the two phase separation system, a soluble fraction as a supernatant is recovered. In the case of using the three phase separation system, it can be separated to three fractions, (1) floating layer (cream fraction with lowest specific weight including fat), (2) mid layer (water-soluble fraction including a small amount of fat and large amounts of protein and sugar) and (3) precipitate layer (insoluble fraction including large amounts of fat and fiber). In this case, soluble fraction, mid layer (2) is recovered.

Reduced-Fat Soymilk

The obtained soluble fraction can be the reduced-fat soymilk used in the present invention as is, or after subjecting to concentration step, heat pasteurization step and powderization step as necessary.

Soybean Protein Isolate

Soybean protein isolate with high purity of protein can be prepared by removing soybean whey component such as whey protein and oligosaccharide from the obtained reduced-fat soymilk and concentrating protein, and if necessary, further subjecting to neutralization, pasteurization, drying and powderization. As for a method of removing soybean whey component, any well known method can be used. For example, as most common method, a method including, adjusting pH of the reduced-fat soymilk to acidic pH nearby isoelectric point (pH about 4 to 5) to isoelectric precipitate, and subjecting the mixture to centrifuge to remove whey as supernatant and recover the precipitate, can be applied. In addition, a method of removing whey having relatively low molecular weight by membrane separation can be applied.

(Feature of the Reduced-Fat Soybean Protein Material)

Although a raw material is fat-containing soybean, this reduced-fat soybean protein material has protein content same as a defatted soymilk or a soybean protein isolate obtained by extracting defatted soybean defatted by using organic solvent such as hexane. However, component other than protein of the reduced-fat soybean protein material is significantly different from that of conventional reduced-fat soybean protein material.

As contrast with defatted soymilk and soybean protein isolate which are obtained by water extraction of defatted soybean defatted with hexane or the like, this reduced-fat soybean protein material has low content of fat, especially polar lipid, and low calories. In addition, because organic solvent such as hexane is not used, the present invention results in less environmental burden and the reduced-fat soybean protein material has significantly fine taste in absence of a denaturation with organic solvent. In addition, the reduced-fat soybean protein material is characterized by showing high oxidation stability and less taste deterioratione with time because polar lipid and LP content is low. Especially, taste-preservation stability is significantly excellent in the case of drying and using as powdered material because fat oxidization does not occur unlike conventional soymilk powder and powdered soybean protein.

<Soybean-Derived Raw Material-Containing Food or Beverage>

In a broad sense, a soybean-derived raw material-containing food or beverage of the present invention encompasses food in which soybean-derived raw material is used as a milk substitute composition, an egg white substitute composition, a composition for improving renal function as described in the following first to third aspects of the present invention.

Hereinafter, each of embodiments of the first to third aspects of the present invention of which special technical feature is this reduced-fat soybean protein material will be described more specifically.

<Embodiment of the First Aspect of the Invention>
(Milk Substitute Composition)

This reduced-fat soybean protein material itself used in the first aspect of the invention can be a milk substitute composition of the first aspect of the invention as various forms such as powder (powdered whole fat milk, powdered skim milk, partially defatted powdered milk, casein protein etc.), concentrate (evaporated milk, condensed milk etc.), liquid (whole milk, low fat milk).

In addition, it can be various forms of milk substitute composition by properly adding other food ingredients or food additives to this reduced-fat soybean protein material.

Addition of Fat

A milk substitute composition of the first aspect of the invention can be prepared as whole fat milk type, partially defatted milk type or cream type by adding fat to this reduced-fat soybean protein material, if necessary, further adding emulsifier to prepare oil-in-water emulsion. Example of the added fat includes animal fat and vegetable fat such as palm oil, coconut oil, palm kernel oil, corn oil, soybean oil, cottonseed oil, rapeseed oil, rice oil, sunflower seed oil, safflower oil, beef tallow, milk fat, lard, cacao butter, fish oil and whale oil, and processed fat thereof obtained by subjecting to one or more treatment selected from hydrogenation, fractionation and interesterification. These fats can be used alone or in any combination of two or more of fats. A content of the fat is preferably 1 to 50 wt %, more preferably 5 to 20 wt % relative to the milk substitute composition in terms of dry basis.

As an emulsifier, natural emulsifier such as lecithin and synthetic emulsifier described later can be used. The synthetic emulsifier includes, for example, glycerol fatty acid ester, glycerol acetic acid fatty acid ester, glycerol lactic acid fatty acid ester, glycerol succinic acid fatty acid ester, glycerol diacetyltartaric acid fatty acid ester, sorbitan fatty acid ester, sucrose fatty acid ester, sucrose acetic acid isobutyric acid ester, polyglycerin fatty acid ester, polyglycerin condensed ricinoleic acid ester, propylene glycol fatty acid ester, sodium stearoyl lactylate, polyoxyethylene sorbitan monostearate, polyoxyethylene sorbitan monoglyceride and the like. A content of the emulsifier is preferably 0.5 to 10 wt %, more preferably 1 to 5 wt % relative to the milk substitute composition in terms of dry basis.

Addition of Sugar

A milk substitute composition of the first aspect of the invention can be prepared as sweetened type such as sweetened condensed milk and whipping cream by adding sugar to this reduced-fat soybean protein material. Example of the added sugar includes monosaccharide such as glucose and galactose; disaccharide such as sucrose, lactose, maltose and trehalose; trisaccharide such as maltotriose and raffinose; oligosaccharide; sugar alcohol such as erythritol, maltitol and lactitol; and the like. These sugars can be used alone or in any combination of two or more of sugars. A content of the sugar is preferably 1 to 50 wt %, more preferably 3 to 20 wt % relative to the milk substitute composition in terms of dry basis.

Other Raw Materials

If necessary, starch, inorganic salt, organic salt, gelling agent, polysaccharide thickener, flavor, taste improver such as seasoning, coloring agent, preserving agent, antioxidant, pH adjuster and the like can be added to the milk substitute composition of the first aspect of the invention. A content of these ingredients is preferably 10 wt % or less relative to the milk substitute composition in terms of dry basis.

(Milk Substitute Food or Beverage)

A milk substitute food or beverage of the first aspect of the invention refers to a food in which a part or all of milk raw material which is commonly used for the food or beverage is substituted with the above milk substitute composition. It is not limited by a subjective purpose of a skilled person in the art whether it is substituted or not. But, it is interpreted from an objective standpoint whether a substitution is eventually occurred. Substitution ratio of the milk substitute composition to milk is not limited. When higher ratio of vegetable ingredient with higher substitution ratio is desired, the ratio can be preferably 50 wt % or more, 70 wt % or more or 90 wt % or more. Especially, when the ratio is 100 wt %, a fully plant-derived milk substitute food or beverage can be prepared and it is suitable for milk-allergic patient. Typical example of a product with 100 wt % of substitution ratio includes soymilk product such as soy milk and lactic acid fermented soymilk. In addition, for a purpose of maintaining milk taste and reducing cost, the substitution ratio can be 50 wt % or less, 30 wt % or less or 10 wt % or less.

An adding amount of the milk substitute composition is not particularly limited because it may vary based on a form of the food or beverage, but can be about 1 to 100 wt %, preferably 10 to 95 wt % relative to the milk substitute food or beverage of the first aspect of the invention in terms of dry basis.

Hereinafter, typical aspects of the milk substitute food or beverage (embodiments of a product in which milk raw material is used) are described. However, it goes without saying that the food or beverage is not limited to the following aspects. The milk substitute food or beverage can be produced with a well known method such as conventionally used method except for substituting a part or all of milk raw material with the milk substitute composition.

Dairy Product

A dairy product includes liquid milk such as composition-adjusted milk, low-fat milk, fat-free milk and high-fat milk; milk beverage containing various nutrients, coffee, cocoa, fruit juice, fruit or the like; fermented milk such as yogurt and yogurt drink; lactic acid bacteria beverage; cream such as whipping cream, whitener, sour cream, powdered cream and custard; ice cream such as ice cream, lacto-ice (ice cream with milk-solids content of 3% or greater) (mellorine) and soft-serve ice cream; cheese such as process cheese, natural cheese and powdered cheese; margarine; powdered milk such as skim milk, baby formula and sweetened powdered milk; and condensed milk such as sweetened condensed milk and unsweetened condensed milk. These dairy products are also used as raw material of other milk substitute foods or beverages.

Sauce

A sauce includes bechamel sauce (white sauce), mornay sauce, aurora sauce, nantua sauce, cream sauce, mustard sauce, soubise sauce, cheese sauce, hollandaise sauce, pasta sauce such as carbonara sauce and the like in which milk raw material is generally used.

Bakery Product

A bakery product includes bread such as white bread, butter roll, Danish pastry, melonpan, muffin and pizza crust; baked confectionery such as sponge cake, pie, butter cake, cheese cake, pancake, Castella (A type of sponge cake in Japan), waffle, chou pastry, savarin, cookie, biscuit, cracker, wafer, nutrition bar, hardtack, rice cracker, sticky rice cracker and baked bun.

Confectionery

A confectionery includes the above mentioned baked confectionery and western confectionery, Chinese-style confectionery and Japanese-style confectionery in which dairy product is generally used, for example, dessert such as pudding, bavarois, jelly and brulee, caramel candy, soft candy, hard candy, candy, tablet, jelly, marshmallow, bonbon, dragee, chocolate, doughnut, steamed bun, flied bun and snack.

Other Processed Foods or Beverages

In addition, the overall processed foods or beverages in which milk raw material is generally used are included. For example, gratin, doria (a rice casserole with white sauce), cream croquette, stew, soup, curry, filling, and protein powder, protein drink, protein jelly, meat product, fishery product, noodle, soft drink, carbonated drink, powdered beverage, baby food and the like are included.

High Nutrient Liquid Food

In the first aspect of the invention, high nutrient liquid food is a nutraceutical product which is used for person who is difficult to receive nourishment from regular diet, for example, some post-surgical patient and aged person with chewing and swallowing difficulties. The high nutrient liquid food includes protein, carbohydrate, fat, mineral and vitamin in a comprehensive manner, and is also called as fluid diet.

More specifically, the liquid food includes protein, lipid, carbohydrate, mineral and vitamin, and is in a form of solution at ordinary temperature and has a caloric value of 0.5 kcal/ml or more. Preferably, it has energy composition of 10% to 25% of protein, 15% to 45% of lipid, and 35% or more of carbohydrates, and a composition of 20 to 110 mg/100 kcal of calcium and 10 to 70 mg/100 kcal of magnesium. More preferably, it has energy composition of 16% to 20% of protein, 20% to 30% of lipid, and 50% to 65% of carbohydrates, and a composition of 35 to 65 mg/100 kcal of calcium and 15 to 40 mg/100 kcal of magnesium.

In many cases, milk raw material such as milk protein, whey protein and casein sodium is generally used as a protein raw material in the high nutrient liquid food. According to the first aspect of the invention, this reduced-fat soybean protein material can be used as substitution for a part or all of the milk raw material.

A taste of the obtained high nutrient liquid food is comparable with that of high nutrient liquid food prepared from milk raw material only, and is significantly better than that of high nutrient liquid food prepared from conventional soymilk or soybean protein isolate.

In addition, when the reduced-fat soybean protein material such as this reduced-fat soymilk is used for the high nutrient liquid food, characteristic of lower reactive property with divalent metal such as calcium and magnesium in the formulation than soybean protein isolate is obtained. Therefore, these metals can be added at high concentration.

Lactic Acid-Fermented Soybean Food or Beverage

In general, lactic acid-fermented soybean food or beverage is prepared by fermenting soybean protein material as a protein source, such as soymilk, soybean protein isolate and soy flour, with lactic acid bacterium similar to fermented milk. And, it is milk substitute food or beverage corresponding to fermented milk such as yogurt and fermented milk product such as lactic acid bacteria beverage and cheese. Recently, taste of conventional soybean protein material having peculiar taste of raw vegetation has been partly improved with an advancement of production technology. However, even if such a taste-improved soybean protein material is used, peculiar acidic precipitation smell which is generated by precipitating soybean protein with acidification is generated by carrying out fermentation with lactic acid bacteria. In addition, even if good fermented taste similar to yogurt or cheese can be obtained immediately after production, the taste will be deteriorated over time. Further, taste may also be deteriorated by heating pasteurization treatment after fermentation. And, such deteriorated taste has a big influence on the quality of product even if a part of milk raw material is substituted. Thus, in order to suppress the taste deterioration, advanced production technique is required, for example, fermentation is carried out with combining specific lactic acid bacteria, fermentation is carried out under no oxygen condition, or the obtained product immediately after fermentation is sealed into container with extremely low oxygen permeability etc. as disclosed in JP 3307255 B, JP 3327155 B, JP 3498551 B or JP H11-75688 A. Therefore, there are some problems, for example, specific lactic acid bacterium strain having desirable physiology cannot be used, investment of new fermentation equipment is necessary, etc. Thus, one of the problems of the first aspect of the invention is to provide a lactic acid-fermented soybean food or beverage which shows little taste deterioration after fermentation regardless of a kind of lactic acid bacterium and a production equipment.

By using this reduced-fat soybean protein material used in the first aspect of the invention as a raw material of a lactic acid-fermented soybean food or beverage, taste deterioration with time can be suppressed in addition to that the raw material itself has superior taste than conventional soybean protein material. Therefore, this reduced-fat soybean protein material used in the first aspect of the invention, which has excellent quality as a milk substitute composition, enables to produce lactic acid-fermented soybean food or beverage having good taste both immediately after fermentation and taste stability with time even if lactic acid bacterium and production equipment which are generally used for conventional yogurt, lactic acid bacteria beverage, cheese or the like are used without using known advanced technique as above mentioned.

Other raw material and production condition of the first aspect of the invention are not particularly limited, and well known material and condition are applicable. An aspect of the production is exemplified as follows.

Major raw material of the lactic acid-fermented soybean food or beverage of the first aspect of the invention includes this reduced-fat soybean protein material used in the first aspect of the invention, lactic acid bacterium, and if necessary, assimilable sugar. An adding amount of this reduced-fat soybean protein material is preferably 50 to 100 wt %, preferably 60 to 100 wt % relative to protein content in the raw material.

In addition, fat, starch, polysaccharide thickener, gelling agent, emulsifier, flavor, acidulant, antioxidant, chelating agent and the like can be added. In the case of a milk substitute food or beverage in which a part of milk is substituted, milk raw material which is used for yogurt or lactic acid bacteria beverage can also be used.

In the case of lactic acid fermentation, it is not necessary to add assimilable sugar as a nutrient source of microorganism to fermentation raw material. However, it is preferable to add when fermentation is hard to progress. For example, glucose, fructose, sucrose, maltose, galactose, lactose, raffinose, trehalose, soybean oligosaccharide, fructo-oligosaccharide, xylo oligosaccharide and the like can be used. These sugar materials can be used alone or in combination of two or more kinds. An adding amount of the assimilable sugar relative to a dry matter of this reduced-fat soybean protein material is preferably 1 to 50 wt %, preferably 5 to 40 wt %.

Lactic acid bacterium to be used in lactic acid fermentation is not particularly limited as long as the lactic acid bacterium can be used for fermented milk product such as yogurt, lactic acid bacteria beverage and cheese. An adding amount of lactic acid bacterium is preferably 0.5 to 15 wt %, preferably 1 to 10 wt % in the case of powdered starter. As lactic acid bacterium, for example, genus *Lactobacillus* such as *Lactobacillus casei, Lactobacillus plantarum, Lactobacillus helveticus, Lactobacillus bulgaricus, Lactobacillus gasseri, Lactobacillus acidophilus, Lactobacillus lactis, Lactobacillus salivarius* subsp. *salivarius, Lactobacillus gallinarum, Lactobacillus amylovorus, Lactobacillus brevis* subsp. *brevis, Lactobacillus fermentum, Lactobacillus mali, Lactobacillus delbrueckii, Lactobacillus johnsonii, Lactobacillus sanfranciscensis, Lactobacillus panex, Lactobacillus comoensis, Lactobacillus italicus, Lactobacillus leichmannii, Lactobacillus curvatus, Lactobacillus hilgardii, Lactobacillus reuteri, Lactobacillus pastorianus, Lactobacillus buchneri, Lactobacillus cellobiosus, Lactobacillus fructivorans* and *Lactobacillus lactis* subsp. *cremoris*; genus *Streptococcus* such as *Streptococcus thermophilus, Streptococcus lactis* and *Streptococcus diacetylactis*; genus *Lactococcus* such as *Lactococcus lactis* subsp. *lactis, Lactococcus lactis* subsp. *cremoris, Lactococcus lactis* subsp. *diacetylactis* and *Lactococcus lactis* subsp. *lactis biovar diacetylactis*; and genus *Leuconostoc* such as *Leuconostoc mesenteroides* subsp. *cremoris, Leuconostoc lactis* and *Leuconostoc pseudomesenteroides* can be used. In addition, a starter in which microorganism other than lactic acid bacterium, for example, yeast such as kefir yeast, is mixed can also be used.

In the first aspect of the invention, genus *Bifidobacterium* is also included in the lactic acid bacterium. For example, *Bifidobacterium bifidum, Bifidobacterium longum, Bifidobacterium infantis, Bifidobacterium breve, Bifidobacterium adolescentis, Bifidobacterium angulatum, Bifidobacterium catenulatum, Bifidobacterium pseudocatenulatum, Bifidobacterium dentium, Bifidobacterium globosum, Bifidobacterium pseudolongum, Bifidobacterium cuniculi, Bifidobacterium choerinum, Bifidobacterium animalis, Bifidobacterium thermophilum, Bifidobacterium bourn, Bifidobacterium magnum, Bifidobacterium asteroides, Bifidobacterium indicum, Bifidobacterium gallicum, Bifidobacterium lactis, Bifidobacterium inopinatum, Bifidobacterium denticolens, Bifidobacterium pullorum, Bifidobacterium suis,*

*Bifidobacterium gallinarum, Bifidobacterium ruminantium, Bifidobacterium merycicum, Bifidobacterium saeculare, Bifidobacterium minimum, Bifidobacterium subtile, Bifidobacterium coryneforme* and the like can be used. In addition, these lactic acid bacteria can be used alone or in any combination of two or more of bacteria.

Especially, specific strain which is used for commercially available yogurt or lactic acid bacteria beverage, or well known, for example, *Lactobacillus casei* (strain YIT 9029 (strain Shirota), strain YIT 10003, strain NY 1301, strain SBR 1202), *Lactobacillus mali* strain YIT 0243, *Lactobacillus acidophilus* (strain SBT-2062, strain CK 92), *Lactobacillus helveticus* strain CK 60, *Lactobacillus gasseri* (strain SP (SBT 2055SR), strain LG 21, strain LC 1, strain OLL 2716, FERMP-17399 etc.), *Lactobacillus delbrueckii* subsp. *bulgaricus* (strain OLL 1023, strain OLL 1029, strain OLL 1030, strain OLL 1043, strain OLL 1057, strain OLL 1073R-1, strain OLL 1075, strain OLL 1083, strain OLL 1097, strain OLL 1104, strain OLL 1162, strain 2038), *Lactobacillus johnsonii* strain La 1 (strain LC 1), *Lactobacillus* strain GG, *Streptococcus thermophilus* (strain 1131, strain OLS 3059), *Bifidobacterium breve* (strain Yakult, strain YIT 4065), *Bifidobacterium bifidum* (strain Yakult), *Bifidobacterium longum* (strain SP (SBT 2928), strain BB 536, Strain BE 80, strain FERM BP-7787), *Bifidobacterium lactis* (strain FK 120, strain LKM 512, strain Bb-12) and the like, can be suitably used.

A condition of lactic acid fermentation can be changed according to the kind of using lactic acid bacterium, for example, it can be carried out at 20 to 50° C., preferable 25 to 45° C. of fermentation temperature. In the case of cheese, fermentation can be carried out at relatively low temperature, at 10 to 50° C., preferably 15 to 45° C. Fermentation time can be, for example, 4 to 72 hours, preferably 5 to 60 hours. Lactic acid fermentation can be carried out until pH of the fermentation raw material is lowered to 3 to 6, if necessary 3 to 5. In addition, pH can also be fine-adjusted to desired pH by using alkali, organic acid or inorganic acid. When pH is too low, acidic taste is too strong and coarse texture tends to occur. When pH is too high, sour taste due to acidification is too weak, in particular, fermented taste is poor in the case of lactic acid fermentation. Fermentation equipment can be carried out with same equipment as that used for producing yogurt or cheese from milk.

After the lactic acid fermentation, stirring and cooling, the obtained product as is can be filled in a container and sealed to make a soft yogurt-type fermented soymilk. Alternatively, raw material can be filled in a container before fermentation, and then subjected to lactic acid fermentation, cooling and sealing to make a hard yogurt-type fermented soymilk. In addition, a drink yogurt-type fermented soymilk or lactic acid bacteria beverage-type fermented soymilk can be prepared by homogenizing the fermented product, and then, if necessary, subjecting to heat pasteurization and cooling, and then filling in a container and sealing. If necessary, various kinds of flavor, coloring agent, stabilizer or fruit preparation can be added before or after the fermentation.

In addition, the lactic acid fermented product can be subjected to a process of separating curd and whey by a centrifuge or the like and recovering the curd to obtain a whey separated type lactic acid-fermented soybean food or beverage. The obtained food or beverage has less unpleasant taste such as fermented smell and acetic acid smell compared to a product prepared from conventional soymilk or soybean protein isolate as a raw material. Especially, whey separated type soy cheese has reduced acidic taste and increased rich taste.

In this case, after the lactic acid fermentation, if necessary, salt such as chloride such as sodium chloride and potassium chloride and phosphate such as sodium polyphosphate can be added to the fermented product before separating whey or the curd obtained by removing whey from the fermented product. These additives can also be added before the lactic acid fermentation.

Especially, it is preferable to add polymer phosphate such as sodium polyphosphate because acidic taste can be reduced and rich taste can be further enhanced, coarse texture can be reduced and smooth texture can be increased by adding phosphate. An adding amount of the phosphate is not particularly limited, but preferably 0.5 to 15 wt % relative to protein in the lactic acid-fermented soybean food or beverage. When amount of phosphate is too low, the effect of reducing coarse texture is reduced. When amount of phosphate is too high, astringency tends to be strong.

A milk substitute food or beverage of the first aspect of the invention can be provided as fat-free or low fat food or beverage because a fat content of this reduced-fat soybean protein material used in the first aspect of the invention is low, can also be almost 0 wt %. More specifically, fat-free or low fat means that fat content of the food or drink is 0 wt % to 3 wt %, preferably, 0 wt % to 1.5 wt %. For example, fat-free or low fat whitener, cream, lactic acid-fermented soybean food or beverage and the like can be provided.

<Embodiment of the Second Aspect of the Invention>
(Egg White Substitute Composition)

This reduced-fat soybean protein material itself used in the second aspect of the invention can be an egg white substitute composition of the second aspect of the invention as various forms such as powder, concentrate, liquid. It is preferable that the soybean protein material is soymilk or soybean protein isolate.

An egg white substitute composition used in the second aspect of the invention is various kinds of edible food composition prepared by using this reduced-fat soybean protein material, which has various kinds of function of egg white, that is, gelling property, emulsifiability, foamability, and the like. More specifically, the composition is an edible food composition such as oil-in-water emulsion, solution containing air bubble, fluid containing air bubble and gel-like material. Various kinds of ingredient other than this reduced-fat soybean protein material can be added to the composition. For example, fat, sugar, protein, mineral, and emulsifier, flavor, coloring agent and the like can be used.

Fat

A fat used in an egg white substitute composition of the second aspect of the invention includes animal fat and vegetable fat such as palm oil, coconut oil, palm kernel oil, corn oil, soybean oil, cottonseed oil, rapeseed oil, rice oil, sunflower seed oil, safflower oil, beef tallow, milk fat, lard, cacao butter, fish oil and whale oil, and processed fat thereof obtained by subjecting to one or more treatment selected from hydrogenation, fractionation and interesterification.

Sugar

A sugar added to an egg white substitute composition of the second aspect of the invention includes monosaccharide such as glucose and galactose; disaccharide such as sucrose, lactose, maltose and trehalose; trisaccharide such as maltotriose and raffinose; oligosaccharide; sugar alcohol such as erythritol, maltitol and lactitol; and the like. In addition, polysaccharide such as various kinds of starch from corn, rice, wheat, potato, sweet potato, cassava and the like, dextrin and modified starch can be used. These sugars can be used alone or in any combination of two or more of sugars in the second aspect of the invention.

Protein

A protein used in an egg white substitute composition of the second aspect of the invention includes milk protein such as whole fat milk, defatted milk and casein; soybean protein such as soymilk, soybean protein concentrate and soybean protein isolate; gluten such as wheat, rice and corn; egg protein such as whole egg, egg white and egg yolk.

Emulsifier

As an emulsifier used in an egg white substitute composition of the second aspect of the invention, natural emulsifier such as lecithin and synthetic emulsifier described later can be used. The synthetic emulsifier includes, for example, glycerol fatty acid ester, glycerol acetic acid fatty acid ester, glycerol lactic acid fatty acid ester, glycerol succinic acid fatty acid ester, glycerol diacetyltartaric acid fatty acid ester, sorbitan fatty acid ester, sucrose fatty acid ester, sucrose acetic acid isobutyric acid ester, polyglycerin fatty acid ester, polyglycerin condensed ricinoleic acid ester, propylene glycol fatty acid ester, sodium stearoyl lactylate, polyoxyethylene sorbitan monostearate, polyoxyethylene sorbitan monoglyceride and the like.

Other Raw Materials

If necessary, inorganic salt, organic salt, gelling agent, polysaccharide thickener, flavor, taste improver such as seasoning, coloring agent, preserving agent antioxidant, pH adjuster and the like can be added to the egg white substitute composition of the second aspect of the invention. A content of these ingredients is preferably 10 wt % or less relative to the egg white substitute composition of the second aspect of the invention in terms of dry basis.

Oil-in-Water Emulsion

An oil-in-water emulsion is prepared by adding the above mentioned various kinds of fat to an aqueous solution of egg white substitute composition in which this reduced-fat soybean protein material is used. It is preferable for emulsifying to add the above mentioned emulsifier and the like. It is preferable that an amount of the fat is 1 to 30 times, preferably 5 to 15 times of an amount of protein in this reduced-fat soybean protein material. It is preferable that homogenization is carried out after adding the fat to prepare emulsion with about 5 ?m of diameter.

Solution Containing Air Bubble or Fluid Containing Air Bubble

A solution containing air bubble or a fluid containing air bubble is prepared by foaming an egg white substitute composition in which this reduced-fat soybean protein material is used. An aqueous solution of the egg white substitute composition is solution or fluid by changing its state depending on concentration of this reduced-fat soybean protein material, degree of foaming and amount of other ingredients. It is preferable that the aqueous solution is about 5 wt %, preferably about 1 to 10 wt % of this reduced-fat soybean protein material solution. It may be preferable to add the above mentioned emulsifier to improve foamablity, foam stability and the like. In addition, it is also effective to add sugar. In this case, an adding amount is preferably 1 to 50 wt %, more preferably 3 to 20 wt % relative to the egg white substitute composition in terms of dry basis.

Gel-Like Material

A gel-like material can be obtained by heating an egg white substitute composition in which this reduced-fat soybean protein material is used. In this case, it is preferable that various kinds of other raw material are added. It is preferable that the aqueous solution is about 1 to 40 wt %, preferably about 10 to 30 wt % of this reduced-fat soybean protein material solution. In addition, it can be used in combination with the above mentioned sugar, fat, protein and other materials, for example, gelling agent such as gelatin, agar, carrageenan and alginate, flavor, coloring agent, inorganic salt, organic salt and the like.

(Egg White Substitute Food or Beverage)

An egg white substitute food or beverage of the second aspect of the invention refers to a food in which a part or all of egg white raw material which is commonly used for the food or beverage is substituted with the above egg white substitute composition. More specifically, it is meringue, dressing, mayonnaise, gel-like food or bakery product such as confectionery. It is not limited by a subjective purpose of a skilled person in the art whether it is substituted or not. But, it is interpreted from an objective standpoint whether a substitution is eventually occurred. Substitution ratio of the egg white substitute composition to egg white is not limited. When higher ratio of vegetable ingredient with higher substitution ratio is desired, the ratio can be preferably 50 wt % or more, 70 wt % or more or 90 wt % or more. Especially, when the ratio is 100 wt %, a fully plant-derived egg white substitute food or beverage can be prepared and it is suitable for egg white-allergic patient. In addition, for a purpose of maintaining egg white taste and reducing cost, the substitution ratio can be 50 wt % or less, 30 wt % or less or 10 wt % or less.

An adding amount of the egg white substitute composition is not particularly limited because it may vary based on a form of the food or beverage, but can be about 1 to 100 wt %, preferably 10 to 95 wt % relative to the egg white substitute food or beverage of the second aspect of the invention in terms of dry basis.

Hereinafter, typical aspects of the egg yolk substitute food or beverage (embodiments of a product in which egg yolk raw material is used) are described. However, it goes without saying that the food or beverage is not limited to the following aspects. The egg yolk substitute food or beverage can be produced with a well known method such as conventionally used method except for substituting a part or all of egg white raw material with the egg white substitute composition.

Meringue-Like Food

Standard meringue-like food refers to a thing prepared by whipping egg white after adding oligosaccharide or a confectionery prepared by using the thing. In the second aspect of the invention, a thing prepared similar to standard meringue except that the egg white substitute composition in which this reduced-fat soybean protein material is used and confectionery prepared by baking the thing are called as a meringue-like food. In addition, it can be added to coffee or the like with whipping without adding oligosaccharide.

Dressing-Like Food, Mayonnaise-Like Food

Dressing-like food and mayonnaise-like food in the second aspect of the invention refer to a food prepared by adding fat and various food materials with using the egg white substitute composition in which this reduced-fat soybean protein material is used, and then preparing oil-in-water emulsion.

Gel-Like Food

A gel-like food in the second aspect of the invention mainly includes various kinds of dessert. These are not limited to puddings in which gelling property of egg white is used, but include jelly, mousse and the like. In addition, the food includes daily dish such as chawan-mushi (steamed egg hotchpotch) and tamago-tofu (steamed egg custard), ham, sausage, fishery product, noodle and the like for which an improvement of physical property is intended.

Confectionery

A confectionery in the second aspect of the invention includes a bakery product prepared from the above mentioned egg white substitute composition or meringue in which the composition is used. More specifically, langue de chat, tuile, financier, awayuki (confection of meringue jellified with agar), tube cake, icing, macaroon, dacquoise and the like are included. These are obtainable by adding other raw materials to the egg white substitute composition and then baking the mixture.

<Embodiment of the Third Aspect of the Invention>

The present inventors have found that this reduced-fat soybean protein material used in the third aspect of the invention has strong effect of improving renal function. The effect of improving renal function can be observed by eating an appropriate amount of this reduced-fat soybean protein material. That is, this reduced-fat soybean protein material used in the third aspect of the invention can be used as an action body of composition for improving renal function.

A content of this reduced-fat soybean protein material in the composition for improving renal function of the third aspect of the invention is 1 to 100 wt %, preferably 50 to 100 wt %, more preferably 80 to 100 wt %, most preferably 100 wt %.

In addition, a food having an effect of improving renal function can be produced by adding an appropriate amount of the composition for improving renal function of the third aspect of the invention to food. Preparing a "food having an effect of improving renal function" without difficulty can be introduced for the first time by that the composition for improving renal function of the third aspect of the invention has both good taste and an effect of improving renal function. That is, it is achieved by the third aspect of the invention for the first time. Further, a food for specified health use or a food for special dietary uses (food for sick person, food for person with dysphagia) having an effect of improving renal function can be prepared by using the composition for improving renal function of the third aspect of the invention.

The process for producing the food having an effect of improving renal function has a technical feature that a "composition for improving renal function" of the third aspect of the invention is included in food.

The above described embodiments of first to third aspects of the invention has common specific technical feature that the above described specific novel reduced-fat soybean protein material is used. It goes without saying that it is possible to be an aspect fusing any two or more of ideas from each technical idea. That is, this reduced-fat soybean protein material can function as, for example, both milk substitute composition and egg white substitute composition, both milk substitute composition and composition for improving renal function, and both egg white substitute composition and composition for improving renal function in a food to be used.

EXAMPLES

Examples of the present invention will be described below. The "%", "parts" described below refers to "wt %", "parts by weight" unless otherwise specified. Measurement of fat is carried out based on the chloroform/methanol mixed solvent extraction method unless otherwise noted.

Production Example 1

Preparation of Reduced-Fat Soymilk A1, A3

To 5 kg of soy flour which was subjected to wet heat treatment to make NSI of 56 was added with 9 times its weight of water at 60° C. to prepare suspension liquid. The suspension liquid was stirred for 30 minutes with keeping warm for water extraction. The pH of the suspension liquid at this time was 6.5. Centrifugation with three phase separation system was continuously carried out at 6,000×g to separate to (1) floating layer, (2) mid layer and (3) precipitate layer. Then, 12 kg of reduced-fat soymilk as the mid layer were recovered. The obtained fraction was lyophilized. And, as general constituent, dry matter, and protein (by Kjeldahl method), fat (by chloroform/methanol mixed solvent extraction method) and ash in terms of dry basis were measured. In addition, LCI value as estimated value of lipoxygenase protein content and LP content was analyzed by SDS-PAGE (see table 2). The obtained reduced-fat soymilk (reduced-fat soymilk A1) was concentrated under vacuum to improve dry matter content to 11.0 wt %. The concentrated product was called as reduced-fat soymilk A2.

Comparative Production Example 1

Preparation of Hexane-Defatted Soymilk B1 and B2

A defatted soymilk (defatted soymilk B1) was prepared in a similar manner of Production Example 1 except that a defatted soy flour (NSI 89) prepared by hexane defatting was used as a raw material soy flour, adding amount of water was 10 times weight, and that extraction time was 30 minutes. The pH of the suspension liquid at extraction was 6.5. This defatted soymilk B1 was concentrated under vacuum to improve dry matter content to 9.3 wt %. The concentrated product was called as reduced-fat soymilk B2.

Comparative Production Example 2

Preparation of Whole Fat Soymilk C

To 1 part of soybean with removing hull and hypocotyl, 10 parts of water was added, and it was immersed at 85° C. for 60 minutes or more to absorb enough water. To 1 part of the water-absorbed soybean with removing hull and hypocotyl (water content: 40 to 55%), 3 parts of hot water (90° C.) was added and the mixture was treated with a grinder, and then sodium bicarbonate solution was added to adjust pH to 7.3 or more and 8.0 or less. This was load to homogenizer (manufactured by APV) to homogenize at 150 kg/cm$^2$. The homogenized ground solution was centrifuged at 3000 G for 5 minutes to obtain soymilk and okara (bean curd refuse). The raw material soy milk (whole fat soymilk) had solid content of 9.0%, protein content of 4.5% and pH of 7.5.

Production Example 2

Preparation of Reduced-Fat Soybean Protein Material (Soybean Protein Isolate)

To 20 kg of soy flour in which NSI was adjusted to 55 was added with 300 kg of water and adjusted to pH 6.5 to prepare suspension liquid. The suspension liquid was stirred at 50° C. for 30 minutes for extraction. Centrifugation was carried out at 1,400×g for 10 minutes to separate to cream layer, mid layer and precipitate layer (okara). Then, soymilk as mid layer was recovered and concentrated to 12% of dry matter, and adjusted to pH 4.5 with adding appropriate amount of hydrochloric acid. The obtained soymilk was subjected to separation with centrifuge at 3,000×g for 15 minutes to recover precipitate.

To the recovered precipitate was added water so that dry matter was 18%, and adjusted to pH 7.5 with adding appropriate amount of sodium hydroxide. The mixture was heat sterilized under pressure and then splay dried to prepare soybean protein isolate.

Analytical result of the obtained soybean protein isolate was, 96.0% of dry matter, 82.1% of protein, 1.90% of total fat (2.31% relative to protein), 6.57% of ash and 9.43% of carbohydrate, in terms of dry basis. In addition, phytosterol content was 10.7 mg per 100 g of dry matter (564 mg per 100 g of fat), and total isoflavone content was 0.301% in terms of dry basis.

Comparative Production Example 3

Preparation of Whole Fat Soymilk D1

A whole fat soymilk D1 was prepared in a similar manner of Production Example 1 except that a standard soy flour was used as a raw material, adding amount of water was 10 times weight, and that extraction time was 30 minutes. The pH of the suspension liquid at extraction was 6.5. This defatted soymilk D1 was concentrated under vacuum to improve dry matter content to 9.3 wt %. The concentrated product was called as whole fat soymilk D2.

Reduced fat soymilk A1 obtained in Production Example 1, reduced-fat soymilk B1 obtained in Comparative Production Example 1, soybean protein isolate obtained in Production Example 2, soybean protein isolate "GPF Meat SPI 6500" (manufactured by Specialty Protein Producers, Inc.), which is believed to be produced by a method described in JP 2009-528847 A, and commercially available soybean protein isolate "Fujipro F" (manufactured by Fuji Oil Co., Ltd.), which is prepared from defatted soybean defatted with hexane, were made as analytical sample. And, as general constituent, dry matter, and protein (by Kjeldahl method), fat (by chloroform/methanol mixed solvent extraction method) and ash in terms of dry basis were measured. In addition, LCI value as estimated value of lipoxygenase protein content and LP content was analyzed by SDS-PAGE. Further, phytosterol content (total content of campesterol and stigmasterol) (mg) per 100 g of fat was analyzed. Each analytical value is shown in table 2. In addition, total content of isoflavone contained in the reduced-fat soymilk obtained in Production Example 1 was measured. As a result, 0.2660 in terms of dry bases was contained.

TABLE 2

| | Dry matter (%) | In terms of dry basis (%) | | | Phytosterol (mg)/100 g fat | LCI |
|---|---|---|---|---|---|---|
| | | Protein | Fat | Ash | | |
| Reduced-fat soymilk A1 (Production Example 1) | 5.0 | 50 | 1.4 (2.8)* | 9.8 | 643 | 32 |
| Reduced-fat soymilk B1 (Comparative Production Example 1) | 6.5 | 67 | 3.5 (5.2) | 6.7 | 42.3 | 43 |
| Soybean protein isolate (Production Example 2) | 96.0 | 82.1 | 1.9 (2.3) | 6.6 | 564 | 33 |
| Commercially available soybean protein isolate GPF Meat SPI 6500 | 95.0 | 86.2 | 10.3 (11.8) | 3.4 | 165 | 43 |
| Commercially available soybean protein isolate Fujipro E | 94.2 | 90.8 | 4.4 (4.8) | 4.5 | 41.5 | 38 |

*Fat contents (%) relative to protein content are in

Specific Example of the First Aspect of the Invention

Hereinafter, the specific examples of producing various kinds of milk substitute food or beverage by using the soybean protein material obtained in Production Example were described.

Example a1

Coffee Whitener

To 60.6 parts of water while heating at 60 to 70° C., 0.4 part of dipotassium phosphate was added and dissolved, and then 18.2 parts of reduced-fat soymilk A2 obtained in Production Example 1, 0.7 part of sugar ester "DX ester F160" (manufactured, by Dai-Ichi Kogyo Seiyaku Co., Ltd.) and 0.5 part of organic acid monoglyceride "Sunsoft 641D" (manufactured by Taiyo Kagaku Co., Ltd.) were added and stirred. After dispersing or dissolving the soymilk and emulsifier in the above solution, 20 parts of refined coconut oil was added to the solution and pre-emulsified.

After the pre-emulsification, the solution was homogenized at 15 MPa by using homogenizer and then loaded to direct high temperature heating apparatus in a steam injection system (manufactured by TANAKA FOOD MACHINERY Co.) and pasteurized at 144° C. for 4 seconds. After the pasteurization, the solution was homogenized at 15 MPa by using homogenizer and then cooled to obtain coffee whitener.

The obtained coffee whitener was added to Kilimanjaro coffee (marketed product) which is one of the high acidic coffees, and the dispersion state was evaluated and the flavor was confirmed. The result was shown in the following.

The dispersion state of coffee whitener was evaluated according to the following basis: a case that aggregation was observed in coffee was assumed to be 5 points, a case that a lot of feathering was observed in coffee was assumed to 4 points, a case that feathering was observed in coffee was assumed to 3 points, a case that feathering was slightly observed in coffee was assumed to 2 points, a case of good that feathering was not observed was assumed to 1 point. In addition, taste evaluation of coffee whitener was carried out by 5 panelists. The taste was evaluated as good when a taste of coffee was not destroyed, and the taste was evaluated as bad when a taste of coffee was destroyed.

TABLE 3

| | Example a1 |
|---|---|
| Dispersion state | 1 |
| Dispersion state (*1) | 1 |
| Taste | good (5/5 panelists) |

(*1) Dispersion state after 1 week storage at 5° C.

The above table suggested that the reduced-fat soymilk of Production Example 1 is suitable as a raw material of whitener for coffee and the like.

Example a2

Fermented Soymilk

To 80 parts of the reduced-fat soymilk A2 obtained in Production Example 1 with heating at 60° C., 5 parts of sugar and 1 part of water-soluble soybean polysaccharide "Soyafive" (manufactured by Fuji Oil Co., Ltd.) with dispersing or dissolving into 14 parts of water was added. The mixture was homogenized at 150 kg/cm² with a homogenizer, and then subjected to heating at 145° C. for 4 seconds with a direct high temperature heating apparatus in a steam injection system (manufactured by TANAKA FOOD MACHINERY Co.). After the pasteurization, the mixture was cooled to 42° C. To the mixture, 1% of individual culture liquids from various commercially available lactic acid bacteria (lyophilized product), *Lactobacillus bulgaricus* and *Streptococcus thermophilus* were respectively added, and fermented at 42° C. for 6 hours, until pH to 4.6. The fermented mixture was cooled to 7° C. while stirring to obtain curd form fermented soymilk. The curd form fermented soymilk was homogenized with stirring and filled to product container.

For a comparison, fermented soymilk was prepared in a similar manner of the above except that defatted soymilk B2 or whole fat soymilk C each obtained in Comparative Production Examples 1 and 2 was used (Comparative Examples a1, a2).

Taste of the obtained each fermented soymilk was evaluated immediately after and 1 week (at 10° C.) after the production. The result was shown in the following table. Taste evaluation was carried out as five-rank evaluation according to the following criteria: 5: palatable, 4: slightly palatable, 3: average, 2: slightly unpalatable, 1: unpalatable.

TABLE 4

|  | Example a2 | Comparative Example a1 | Comparative Example a2 |
| --- | --- | --- | --- |
| Raw material soymilk | Production Example 1 | Comparative Production Example 1 | Comparative Production Example 2 |
| Taste (immediately after the production) | 5 | 1 | 5 |
| Taste (1 week after the production, stored at 10° C.) | 5 | 1 | 2 |

When the fermented soymilk of Example a2 was compared with the fermented soymilk of Comparative Example a2 prepared from whole fat soymilk C, both tastes ware similar immediately after the production, but the fermented soymilk of Example 2 clearly showed better taste and less taste deterioration with time 1 week after the production. The fermented soymilk of Comparative Example a1 prepared from defatted soymilk showed remarkably bad taste. Therefore, it was suggested that the reduced-fat soymilk of the Production Example a1 is more suitable as a raw material of fermented soymilk than whole fat soymilk.

Example a3

Lactic Acid Bacteria Beverage

To 96 parts of reduced-fat soymilk A2 of Production Example 1, 3 parts of glucose was added and dissolved by using a Homomixer. The mixture was pasteurized at 105° C. for 2 minutes with an autoclave, and then cooled to 38° C. Then, *Lactobacillus casei* strain Shirota was added as starter at initial artificial inoculation levels of 6th power of 10/ml, and fermentation was carried out at 38° C. until pH 3.6 as fermentation end-point to obtain curd form fermented product.

Separately, 7.5 parts of polydextrose "Litesse Ultra" (manufactured by Danisco Japan Co.), 11.0 parts of granulated sugar and 0.04 part of aspartame sweetener "PAL SWEET DIET" (Manufactured by Ajinomoto Co., Inc.) was dissolved into warm water by using a Homomixer, and then pasteurized at 105° C. for 1 minute with an autoclave, and then cooled to prepare a syrup.

The curd form fermented product was homogenized to fermented liquid, and mixed with the above syrup at a ratio of 23:77, and homogenized at 15 MPa after adding flavor to obtain lactic acid bacteria beverage. This lactic acid bacteria beverage was good having pleasant fermented taste and sweet taste.

Example a4

High Nutrient Liquid Food

The reduced-fat soymilk A2 obtained in Production Example 1 was formulated according to the formula of the following table with a Homomixer and then loaded to homogenizer (manufactured by APV) to homogenize at 50 MPa. The obtained homogenized liquid was filled into retort pouch and sealed. The retort pouch was laded to retort sterilization equipment (RCS-40RTG, manufactured by Hisaka Works, Ltd.), and treated at 121° C. for 15 minutes to produce a high nutrient liquid food.

For a comparison, a high nutrient liquid food was produced in a similar manner of the above except that casein sodium (Comparative Example a3) or whole fat soymilk C obtained in Comparative Production Example 2 (Comparative Example a4) was substituted for the reduced-fat soymilk. Each nutrient content of the formulation of each Example was same.

TABLE 5

| Formula of Examples | | | |
| --- | --- | --- | --- |
|  | Example a4 | Comparative Example a3 | Comparative Example a4 |
| Casein sodium | — | 5.5 | — |
| Soybean protein isolate (*1) | 3.3 | — | 3.6 |
| Reduced-fat soymilk (Production Example 1) | 39.0 | — | — |
| Whole fat soymilk (Comparative Production Example 2) | — | — | 39.0 |
| Dextrin | 13.5 | 15.0 | 15.0 |
| Rapeseed refined oil | 1.5 | 1.6 | — |
| Mineral mix | 0.8 | 0.8 | 0.7 |
| Emulsifier | 0.3 | 0.3 | 0.3 |
| Crystalline cellulose (*2) | 0.2 | 0.2 | 0.2 |
| Water | Remainder | Remainder | Remainder |
| Total | 100 | 100 | 100 |

(Unit: part(s))
(*1) Proleena(TM) RD-1 (manufactured by Fuji Oil Co., Ltd.)
(*2) Ceolus(TM) RC-N81 (manufactured by Asahi Kasei Chemicals Co.)

Example a4 showed good taste similar to Comparative Example a4, which is in the case of whole fat soymilk, and it was suggested that the reduced-fat soymilk of Production Example 1 can be used as substitute for casein sodium. Example a4 showed suppressed color change after heating similar to Comparative Example a4 and more than Comparative Example a3.

Examples a5-a8

Ice Cream

The reduced-fat soymilk A1 obtained in Production Example 1 and the defatted soymilk B1 obtained in Comparative Production Example 1 were powderized with a spray drier in same condition. Ice creams were prepared by using these soymilk powders according to the following formula with the following procedure.

Warm water and starch syrup were put into stainless container, and heating to 65° C. by using hot water bath, and then, previously measured and mixed raw material powders were added thereto and dissolved by using a tabletop Homomixer (T.K. HOMOMIXER MARK II) at 5,000 rpm for 30 minutes. And then, coconut oil and reduced-fat soymilk were added to the mixture. Finally, water content was adjusted with hot water. The obtained preparation liquid was homogenized at 15 MPa and aged at 5° C. for overnight, and stirred by using Ice creamer (manufactured by SIMAC) until 30% of overrun, and filled into cup, and rapidly cooled with a deep freezer at −80° C. for 1 hour, and then stored at −18° C.

A taste of each obtained ice cream was evaluated.

Margarine and granulated sugar was mixed and whipped (specific weight: 0.69). To the mixture, the reduced-fat soymilk powder was added, and then adding whole egg while emulsifying. Soft wheat flour was added to the mixture and mixed to prepare dough. To pound cake pan with 165 mm long, 65 mm wide and 60 mm high, 300 g of the dough was filled. And then, it was baked with an oven at 180° C. for 45 minutes to obtain pound cake.

For a quality comparison, pound cake was produced in a similar manner as the above except that powdered skim milk generally used for pound cake (Reference Example a1) or the same low fat soymilk powder as Comparative Example a5 (Comparative Example a7) was substituted for the reduced-fat soymilk.

TABLE 6

Formula of Examples

| | Example a5 | Example a6 | Example a7 | Example a8 | Comparative Example a5 | Comparative Example a6 |
|---|---|---|---|---|---|---|
| Reduced-fat soymilk powder (Production Example 1) | 20 | 20 | 30 | 65 | — | — |
| Low fat soymilk powder (Comparative Production Example 1) | — | — | — | — | 1.87 | 6.08 |
| Superfine sugar | 10 | 10 | 5 | 13 | 10 | 13 |
| Brine | — | 0.09 | — | — | — | — |
| Trehalose | 1 | 1 | 1 | — | 1 | — |
| Maltose | — | — | — | 6 | — | 6 |
| Starch syrup | 16 | 16 | 10 | 3.5 | 16 | 3.5 |
| Table salt | 0.05 | 0.05 | 0.05 | — | 0.05 | — |
| Coconut oil | 3 | 3 | — | 4.5 | 3 | 4.5 |
| Polydextrose | — | — | 5.5 | — | — | — |
| Sucralose | — | — | 0.01 | — | — | — |
| Thickening agent(*1) | 0.2 | 0.2 | 0.2 | 0.2 | 0.2 | 0.2 |
| Emulsifier(*2) | 0.2 | 0.2 | 0.2 | 0.2 | 0.2 | 0.2 |
| Water | Remainder | Remainder | Remainder | Remainder | Remainder | Remainder |
| Sensory evaluation | Clear taste | Richer taste than Example a1 | Clear taste | Smooth soybean taste and good rich taste | Prominent soybean taste more than Examples a1, a2 | Too strong soybean taste, bad taste |

(Unit: part(s))
(*1) CESALPINIA LBG LA-200HV (distributed by San-Ei Gen F.F.I., Inc.)
(*2) Homogen(TM) DM (manufactured by San-Ei Gen F.F.I., Inc.)

As shown in the above Comparative Examples a5, a6 in the above table, by using the defatted soymilk powder of Comparative Production Example 1, soybean taste was strong and soybean smell was emphatic at high content. On the other hand, by using the reduced-fat soymilk of Production Example 1, ice cream having smooth soybean taste and rich and good taste could be produced even at high content, 65% (Example a8). In addition, by adding small amount of brine, taste became rich and good (Example a6). Further, by using reduced-fat soymilk without adding fat as shown in Example a7, fat-free ice cream having low caloric value and clear taste.

Examples a9

Pound Cake

Baked confectionery, pound cake was produced by using the same reduced-fat soymilk powder as Example a5 according to the following formula with the following procedure.

TABLE 7

Formula of Examples

| | Example a9 | Reference Example a1 | Comparative Example a7 |
|---|---|---|---|
| Margarine (*1) | 23.8 | 23.8 | 23.8 |
| Granulated sugar | 23.8 | 23.8 | 23.8 |
| Reduced-fat soymilk powder (Production Example 1) | 5.0 | 0 | 0 |
| Low fat soymilk (Comparative Production Example 1) | 0 | 0 | 5.0 |

TABLE 7-continued

Formula of Examples

|  | Example a9 | Reference Example a1 | Comparative Example a7 |
|---|---|---|---|
| Powdered skim milk | 0 | 5.0 | 0 |
| Whole egg | 26.8 | 26.8 | 26.8 |
| Soft wheat flour | 20.6 | 20.6 | 20.6 |
| Taste evaluation | Simple and good soybean taste | Strong milk taste like a condensed milk | Peculiar soybean smell |
| Texture evaluation | Good | Slightly hard, bad good | Bad, and coarse texture |

(Unit: part(s))
(*1) Message(TM) 500 (manufactured by Fuji Oil Co., Ltd.)

The pound cake of Example a9 was better than that of Comparative Example a7 in both taste and texture. And it had a good aptitude for substitution for powdered skim milk in baked confectionery.

Examples a10

Soy Cheese

To 100 parts of the reduced-fat soymilk A2 obtained in Production Example 1, 0.01 part of lactic acid bacterium starter for cheese (manufactured by Christian Hansen A/S) was added, and this was subjected to fermentation at 22° C. for 24 hours. After fermentation, pH was 5.1. Then, sodium hydroxide was added to be pH 5.6, and then heating for pasteurization by boiling to 70° C. while stirring. A part of the obtained fermented product was recovered to obtain whey non-separated type soy cheese.

In addition, the fermented product similarly obtained from the above was centrifuged (9000 rpm×20 minutes) to separate curd and whey, and then the curd was recovered to obtain whey separated type soy cheese.

For a comparison, whey non-separated type soy cheese was obtained in a similar manner as the above except that whole fat soymilk C obtained in Comparative Production Example 2 was substituted for the reduced-fat soymilk A2 (Comparative Example a8).

A taste of the obtained soy cheese was evaluated by 5 expert panelists. As a result, both whey non-separated type and whey separated type had good taste like a cheese with very little unpleasant taste such as fermented smell and acetic acid smell compared to Comparative Example a8.

Examples a11

High Nutrient Liquid Food 2

The reduced-fat soymilk A2 obtained in Production Example 1 was formulated according to the formula of the following table with a Homomixer and then loaded to homogenizer (manufactured by APV) to homogenize at 50 MPa. The obtained homogenized liquid was simply pasteurized at 90° C. to obtain high nutrient liquid food.

For a comparison, a high nutrient liquid food was produced in a similar manner of the above except that commercially available soybean protein isolate was substituted for the reduced-fat soymilk (Comparative Example a9). Each calcium, magnesium content of the formulation of each Example was same.

TABLE 8

Formula of Examples

|  | Example a11 | Comparative Example a9 |
|---|---|---|
| Milk protein (*1) | 2.5 | 2.7 |
| Casein Na | 0.6 | 0.0 |
| Reduced-fat soymilk (Production Example 1) | 38.5 | 0.0 |
| Soybean protein isolate (*2) | 0.0 | 2.9 |
| Dextrin | 13.5 | 15.0 |
| Rapeseed refined oil | 2.1 | 2.1 |
| Magnesium chloride | 0.2 | 0.3 |
| Emulsifier | 0.3 | 0.3 |
| Water | Remainder | Remainder |
| Total | 108 | 108 |

(Unit: part(s))
(*1) Calcium Caseinate 385 (Obtained from Fonterra Japan Co., Ltd.)
(*2) Proleena(TM) RD-1 (manufactured by Fuji Oil Co., Ltd.)

The high nutrient liquid food of Example a11 had dramatically improved taste as compared with Comparative Example a9. In addition, while the high nutrient liquid food of Comparative Example a9 was coagulated like a tofu after heat pasteurization, that of Example 11 had comprehensively good quality that coagulation was not observed and stable state liquid was maintained.

In Example a9, it was presumable that magnesium ion in the formulation was bound to protein to coagulate, and therefore, it was necessary to reduce magnesium content. On the other hand, it was not necessary to reduce magnesium content and possible to add high amount of magnesium in Example a11.

Specific Example of the Second Aspect of the Invention

Example b1

Preparation of Mayonnaise-Like Food

To 48.5 parts by weight of the reduced-fat soymilk A2 prepared in Production Example 1, mixed powder of 1.5 parts by weight of purified salt, 1.5 parts by weight of modified starch ("Yugao" manufactured by Matsutani Chemical Industry Co., Ltd.), 0.05 part by weight of xanthan gum ("Sun Ace", manufactured by San-Ei Gen F.F.I., Inc.) and 1.0 part by weight of seasoning was added and dissolved by stilling with a Homomixer at 70° C. for 10 minutes, then 11.8 parts by weight of rice vinegar was added and 30.0 parts by weight of rapeseed oil was added in a few parts while stirring, and then flavor was added. The mixture was sufficiently stirred, and then rapidly cooled on ice water bath.

Viscosity of them was measured by using a BM-type viscometer with rotor No. 4 at 10° C. and 6 rpm for 1 minute. As a result, the viscosity was 46,000 mPa·s.

The obtained mayonnaise-like food was preferable with low allergenicity. In addition, it showed about 50 kcal per one serve (15 g) and it is about half of common commercially available mayonnaise (about 100 kcal).

Comparative Example b1

A mayonnaise-like food was prepared in a similar condition of Production Example 1. However, whole fat soymilk D2 prepared in Comparative Production Example 2 was used as substitute for the reduced-fat soymilk A2. The mayonnaise-like food obtained in Example b1 had good shape retention property, good emulsion state and good taste compared to Comparative Example b1.

Example b2

Preparation of Meringue-Like Food

A mixture liquid of 150 parts of reduced-fat soymilk A2 prepared in Production Example 1 and 150 parts of granulated sugar was stirred for 10 minutes by using a Kenmix mixer to obtain a meringue-like food. The obtained meringue-like food was baked in an oven at 120° C. for 1 hour to obtain a baked confectionery.

Comparative Example b2

A mixture liquid of 150 parts of whole fat soymilk D2 prepared in Comparative Production Example b2 and 150 parts of granulated sugar was stirred for 10 minutes by using a Kenmix mixer to obtain a meringue. The obtained meringue was baked in an oven at 120° C. for 1 hour to obtain a meringue confectionery.

Comparative Example b3

A mixture liquid of 150 parts of defatted soymilk B2 prepared in Comparative Production Example 1 and 150 parts of granulated sugar was stirred for 10 minutes by using a Kenmix mixer to obtain a meringue. The obtained meringue was baked in an oven at 120° C. for 1 hour to obtain a meringue confectionery.

Whipping state and taste of each meringue-like food obtained in the above was shown in the following table. The whipping state was evaluated according to the following basis: a case that enough whipping was observed was assumed to be 5 points, a case that whipping was observed was assumed to 4 points, a case that a little whipping was observed was assumed to 3 points, a case that little whipping was observed was assumed to 2 points, a case that whipping was not observed was assumed to 1 point. In addition, taste evaluation of baked confectionery was carried out by 5 panelists. Taste was evaluated according to the following criteria: 5: palatable, 4: slightly palatable, 3: average, 2: slightly unpalatable, 1: unpalatable.

TABLE 9

|  | Whipping state | Taste |
| --- | --- | --- |
| Comparative Example b2 | 1 | 5 |
| Comparative Example b3 | 3 | 1 |
| Example b2 | 4 | 5 |

In the case of using the reduced-fat soymilk, whipping was observed in contrast with the case of using whole fat soymilk, and taste was better than the case of using conventional defatted soymilk.

Example b3

Mixing with Egg White

A mixture liquid of 75 parts of reduced-fat soymilk A2, 75 parts of egg white and 150 parts of granulated sugar was stirred for 10 minutes by using a Kenmix mixer to obtain a meringue. The obtained meringue-like food was baked in an oven at 120° C. for 1 hour to obtain a baked confectionery. This was evaluated similar to Example b2.

Example b4

With or without Water-Soluble Soybean Polysaccharide

A mixture liquid of 75 parts of reduced-fat soymilk A2, 75 parts of egg white, 150 parts of granulated sugar and 6 parts of water-soluble soybean polysaccharide "Soyafive-S-DA100" (manufactured by Fuji Oil Co., Ltd.) was stirred for 10 minutes by using a Kenmix mixer to obtain a meringue-like food. The obtained meringue-like food was baked in an oven at 120° C. for 1 hour to obtain a baked confectionery. This was evaluated similar to Example b2.

TABLE 10

|  | Whipping state | Taste |
| --- | --- | --- |
| Example b3 | 4 | 5 |
| Example b4 | 5 | 5 |

Also in the case of using the reduced-fat soymilk and egg white in combination, whipping was observed and taste was good. Therefore, it was suggested that the reduced-fat soymilk can be used as substitution for egg white. In addition, it was suggested that whipping was improved by adding water-soluble soybean polysaccharide.

Example b5

Gel-Like Food

A powdered reduced-fat soybean was prepared by lyophilization of the reduced-fat soymilk A1. To 25 parts of this powder, 75 parts of cold water was added and adjusted the pH to 7.5. Then, the mixture was subjected to defoaming with centrifugation. Then, 4.2 parts of 10 wt % solution of transglutaminase "Activa TG-S" (Manufactured by Ajinomoto Co., Inc.). Then, the mixture was made to slurry and molded, and then heated at 55° C. for 30 minutes, and then further heated for pasteurization at 90° C. for 30 minutes to obtain a gel-like food.

Comparative Example b4

A gel-like food was prepared in a similar manner of Example b5 except that defatted soymilk powder "Profit 1000" (manufactured by Fuji Oil Co., Ltd.) was substituted for the reduced-fat soymilk powder. When both were compared, Example b5 prepared by using the reduced-fat soymilk powder had firm and elastic texture compared to Comparative Example b4.

Example b6

Preparation of Langue De Chat

To 50 g of the reduced-fat soymilk A2, 50 g of sugar was added to prepare fluid containing air bubble like a meringue. Half amount of the obtained meringue-like product was added to 60 g of butter separately kneaded at room temperature and mixed with stirring, and then 50 g of soft wheat flour was added. Further remaining meringue-like product was added to the mixture and stirred. The obtained mixture was squeezed out to baking sheet from nozzle with 1 cm of diameter, and then baked at 120° C. for 4 minutes, and further baked at 170° C. for 10 minutes.

Example b7

Preparation of Tuile

A mixture of 30 g of the reduced-fat soymilk A2 and 30 g of sugar was prepared by stirring and 40 g of soft wheat flour was added and stirred. Further, 40 g of melted butter and vanilla flavoring was added to the obtained mixture and stirred. To the obtained mixture, 50 g of sliced almond was mixed, and then each 5 g of the mixture was spread on baking sheet, and then baked at 170° C. for 10 minutes.

Example b8

Preparation of Financier

To a mixture of 120 g of sugar and 40 g of soft wheat flour, 100 g of the reduced-fat soymilk A2 and 15 ml of rum were added and mixed with stirring. Separately, 100 g of butter was heated in pan to prepare "burnt butter" and then cooled and strained. Both were mixed with stirring and out into mold for financier, and then baked at 170° C. for 25 minutes.

Specific Example of the Third Aspect of the Invention

Example c1, Comparative Example c1

Urinary NAG Activity Reducing Test

Urinary NAG (β-N-acetyl-D-glucosaminidase) was measured after feeding a feed having formulation as shown in table 11 to rat. Damage such as degeneration or destruction of renal tubular epithelial cell can be found by determining urinary NAG level because NAG in serum is hard to pass into urine due to its remarkably large size while NAG is widely distributed in internal organs.

TABLE 11

Feed formulation
g/100 g feed formulation CP20%

| Components | Comparative Example c1 | Example c1 |
|---|---|---|
| Casein | 22.7 | 11.4 |
| Reduced-fat soymilk of Production Example 1 (powder) | — | 33.3 |
| Soybean oil (*) | 20.0 | 0.0 |
| β-corn starch | 24.3 | 22.4 |
| sucrose | 10.0 | 10.0 |
| α-corn starch | 13.2 | 13.2 |
| Cellulose | 5.0 | 5.0 |
| Mineral mix (AIN-93G) | 3.5 | 3.5 |
| Vitamin mix (AIN-93) | 1.0 | 1.0 |
| Choline bitartrate (mL) | 0.3 | 0.3 |
| Total | 100 | 100 |

(*) contains 0.002% TBHQ

Test Method
Animal: Zucker fatty rat
Number of animal, period: n=6×2 groups, 2 weeks
Test sample: Casein, reduced-fat soymilk of Production Example 1 (powder)
Procedure: <Body weight, intake> Measured every day
<Blood sampling> Total 2 times (Interim, at final anatomy)
Analysis: Urinary NAG activity (NAG test Shionogi), urinary protein (Tonein-TP)

Test Result

As for the urinary NAG activity, experimental plot of using the reduced-fat soymilk of Production Example 1 (powder) showed significantly lower value than experimental plot of using casein after 2 weeks feeding. It is known that the Zucker fatty rat is a mutant which shows remarkable obesity, and that nephropathy is developed with aging as coexisting illness.

It was shown that development of nephropathy according to aging of Zucker fatty rat positively suppressed in Example c1 while development of nephropathy according to aging of Zucker fatty rat was not any suppressed by casein-containing feed in Comparative Example c1.

INDUSTRIAL APPLICABILITY

The first aspect to third aspect of the invention can be used for producing various foods in which soybean derived raw material is used as a raw material for various purposes.

For example, consumers can improve their renal function through dietary habit by using a composition for improving renal function according to the third aspect of the invention. Thus, it becomes possible to develop a product that stimulates new demand in the food industry.

The invention claimed is:

1. A process for producing a soybean-derived raw material-containing food or beverage, which comprises substituting at least a portion of the raw material with a composition comprising a reduced-fat soybean protein material,
   wherein the reduced-fat soybean protein material comprises a protein and a carbohydrate at a total content of 80 wt % or more in terms of dry basis, a fat at a content of less than 9 wt % relative to the protein content, and campesterol and stigmasterol as phytosterols at a total content of 230 mg or more relative to 100 g of the fat,
   wherein the reduced-fat soybean material is prepared with a modified soybean having a nitrogen solubility index (NSI) value in the range from 20 to 77,
   wherein the fat content is calculated as a total amount extracted with a mixed solvent of chloroform and methanol at a volume ratio of 2:1 at an atmospheric boiling point for 30 minutes, and
   wherein the raw material is a milk raw material or an egg white, or wherein the food or beverage is for improving renal function.

2. A process for producing a soybean-derived raw material-containing food or beverage, which comprises substituting at least a portion of the raw material with a composition comprising a reduced-fat soybean protein material,
   wherein the reduced-fat soybean protein material comprises a protein and a carbohydrate at a total content of 80 wt % or more in terms of dry basis, a fat at a content of 5 wt % or less in terms of dry basis, and campesterol and stigmasterol as phytosterols at a total content of 230 mg or more relative to 100 g of the fat,
   wherein the reduced-fat soybean material is prepared with a modified soybean having a nitrogen solubility index (NSI) value in the range from 20 to 77,
   wherein the fat content is calculated as a total amount extracted with a mixed solvent of chloroform and methanol at a volume ratio of 2:1 at an atmospheric boiling point for 30 minutes, and
   wherein the raw material is a milk raw material or an egg white, or wherein the food or beverage is for improving renal function.

3. The process according to claim 1, wherein the reduced-fat soybean protein material comprises the fat at a content of less than 8 wt % relative to the protein content.

4. The process according to claim 1, wherein the reduced-fat soybean protein material comprises campesterol and stigmasterol as phytosterols at a total content of 400 mg or more relative to 100 g of the fat.

5. The process according to claim 2, wherein the reduced-fat soybean protein material comprises campesterol and stigmasterol as phytosterols at a total content of 400 mg or more relative to 100 g of the fat.

6. The process according to claim 3, wherein the reduced-fat soybean protein material comprises campesterol and stigmasterol as phytosterols at a total content of 400 mg or more relative to 100 g of the fat.

7. The process according to claim 1, wherein the reduced-fat soybean protein material further comprises isoflavones at a content of 0.1 wt % or more in terms of dry basis.

8. The process according to claim 2, wherein the reduced-fat soybean protein material further comprises isoflavones at a content of 0.1 wt % or more in terms of dry basis.

9. The process according to claim 3, wherein the reduced-fat soybean protein material further comprises isoflavones at a content of 0.1 wt % or more in terms of dry basis.

10. The process according to claim 1, wherein the content of the phytosterols remaining in the reduced-fat soybean protein material from a soybean seed as a starting material is 230 mg or more relative to 100 g of the fat.

11. The process according to claim 2, wherein the content of the phytosterols remaining in the reduced-fat soybean protein material from a soybean seed as a starting material is 230 mg or more relative to 100 g of the fat.

12. The process according to claim 3, wherein the content of the phytosterols remaining in the reduced-fat soybean protein material from a soybean seed as a starting material is 230 mg or more relative to 100 g of the fat.

13. The process according to claim 4, wherein the content of the phytosterols remaining in the reduced-fat soybean protein material from a soybean seed as a starting material is 400 mg or more relative to 100 g of the fat.

14. The process according to claim 5, wherein the content of the phytosterols remaining in the reduced-fat soybean protein material from a soybean seed as a starting material is 400 mg or more relative to 100 g of the fat.

15. The process according to claim 6, wherein the content of the phytosterols remaining in the reduced-fat soybean protein material from a soybean seed as a starting material is 400 mg or more relative to 100 g of the fat.

16. The process according to claim 1, wherein a lipophilic proteins content index (LCI) value of the reduced-fat soybean protein material is 40% or less.

17. The process according to claim 2, wherein a lipophilic proteins content index (LCI) value of the reduced-fat soybean protein material is 40% or less.

18. The process according to claim 1, further comprising fermenting the reduced-fat soybean protein material with lactic acid bacterium.

19. The process according to claim 2, further comprising fermenting the reduced-fat soybean protein material with lactic acid bacterium.

20. A process for producing a soybean-derived raw material-containing food or beverage, which comprises the steps of:
  (1) adding water to
    a modified fat-containing soybean, which comprises, as a raw material, a fat at a content of 15 wt % or more in terms of dry basis and has a nitrogen solubility index (NSI) value in the range from 20 to 70,
    to prepare a suspension liquid;
  (2) subjecting the suspension liquid of the modified fat-containing soybean to a solid-liquid separation to transfer a neutral lipid, a polar lipid and a protein comprising a lipophilic protein as a major component to an insoluble fraction comprising fiber,
  (3) removing the insoluble fraction and recovering a soluble fraction comprising sugar and protein comprising glycinin and β-conglycinin as major components to obtain a reduced-fat soybean protein material, and
  (4) substituting at least a portion of the raw material with a composition comprising the reduced-fat soybean protein material,
    wherein the fat content is calculated as a total amount extracted with a mixed solvent of chloroform and methanol at a volume ratio of 2:1 at an atmospheric boiling point for 30 minutes.

* * * * *